US008702675B2

(12) United States Patent
Imai

(10) Patent No.: US 8,702,675 B2
(45) Date of Patent: Apr. 22, 2014

(54) VIAL ADAPTER

(75) Inventor: Masaomi Imai, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/496,781

(22) PCT Filed: Dec. 3, 2010

(86) PCT No.: PCT/JP2010/071654

§ 371 (c)(1),
(2), (4) Date: Mar. 16, 2012

(87) PCT Pub. No.: WO2011/068190

PCT Pub. Date: Jun. 9, 2011

(65) Prior Publication Data

US 2012/0179129 A1 Jul. 12, 2012

(30) Foreign Application Priority Data

Dec. 4, 2009 (JP) ................................ 2009-276238
Mar. 15, 2010 (JP) ................................ 2010-056877

(51) Int. Cl.
*A61B 19/00* (2006.01)
*A61M 5/32* (2006.01)

(52) U.S. Cl.
USPC .......................................... 604/411; 604/403

(58) Field of Classification Search
CPC ......... A61M 5/162; A61J 1/10; A61J 1/2089; A61J 2001/2013; A61J 2001/201; A61J 1/2096; B65D 51/002
USPC ........ 604/404-416, 905, 403; 403/4, 36, 364, 403/148.23, 324; 285/148.23, 324; 141/2, 141/4, 5, 9, 97, 311 R, 319, 329, 330, 346, 141/363, 364, 365, 366, 369, 383, 384; 215/247, 249
See application file for complete search history.

(56) References Cited

U.S. PATENT DOCUMENTS 5,211,638 A * 5/1993 Dudar et al. .................. 604/539
5,334,179 A 8/1994 Poli et al.

(Continued)

FOREIGN PATENT DOCUMENTS

JP 2005-504609 A 2/2005
JP 2005-516696 A 6/2005

(Continued)

OTHER PUBLICATIONS

International Search Report (PCT/ISA/210) issued on Jan. 11, 2011, by Japanese Patent Office as the International Searching Authority for International Application No. PCT/JP2010/071654.

(Continued)

*Primary Examiner* — Melanie Hand
*Assistant Examiner* — Ned T Heffner
(74) *Attorney, Agent, or Firm* — Buchanan Ingersoll & Rooney PC

(57) ABSTRACT

A vial adapter is provided with a fitting portion which can be fitted into the head portion of a vial, and a hollow needle with a side hole. The base end portion of the needle is provided with a stopper contact portion which contacts the top surface of a stopper when the fitting portion is fitted in the head portion of the vial. When the fitting portion is fitted in the head portion of the vial, the stopper contact portion contacts the top surface of the stopper, and the fitting portion is fixed to the head portion of the vial by a claw engaging with the head portion of the vial, and further, the region of the side hole nearest the base end portion of the needle is positioned either roughly at the bottom surface of the stopper or inside of the stopper.

9 Claims, 17 Drawing Sheets

(56) References Cited

U.S. PATENT DOCUMENTS

| | | | | |
|---|---|---|---|---|
| 5,890,610 | A * | 4/1999 | Jansen et al. | 215/253 |
| 6,715,520 | B2 * | 4/2004 | Andreasson et al. | 141/329 |
| 6,875,205 | B2 | 4/2005 | Leinsing | |
| 6,957,745 | B2 * | 10/2005 | Thibault et al. | 215/249 |
| 7,867,215 | B2 | 1/2011 | Akerlund et al. | |
| 8,122,923 | B2 | 2/2012 | Kraus et al. | |
| 2003/0070726 | A1 | 4/2003 | Andreasson et al. | |
| 2003/0153895 | A1 | 8/2003 | Leinsing | |
| 2003/0199847 | A1 | 10/2003 | Akerlund et al. | |
| 2007/0079894 | A1 | 4/2007 | Kraus et al. | |
| 2007/0106244 | A1 * | 5/2007 | Mosler et al. | 604/411 |
| 2007/0156112 | A1 * | 7/2007 | Walsh | 604/415 |

FOREIGN PATENT DOCUMENTS

| | | | |
|---|---|---|---|
| JP | 2005-522282 | A | 7/2005 |
| JP | 2007-509691 | A | 4/2007 |
| JP | 2008-006066 | A | 1/2008 |

OTHER PUBLICATIONS

Written Opinion (PCT/ISA/237) issued on Jan. 11, 2011, by Japanese Patent Office as the International Searching Authority for International Application No. PCT/JP2010/071654.

* cited by examiner

VIAL ADAPTER

TECHNICAL FIELD

The present invention relates to a vial adapter connected to a vial for transferring a liquid chemical contained in the vial into a syringe.

BACKGROUND ART

In general, at the time of taking out a liquid chemical from a vial, a metallic injection needle is made to directly puncture a rubber stopper (stopper) of the vial and the liquid chemical is sucked out. However, troubles such as accidental sticking with the injection needle or leakage of the liquid chemical via a gap between the injection needle and the rubber stopper may occur. Especially, when the liquid chemical is a dangerous drug such as a carcinostatic agent, leakage of the liquid chemical poses a risk of damaging the health of the person who prepares the drug. In view of this, in recent years, vial adapters permitting easy drug preparation without leakage of the drug to the exterior have been proposed. Examples of general vial adapters in the conventional technique have included a vial adapter, which includes a fitting portion having a plurality of claws for fitting a vial therein, a metallic or resin made (plastic-made) needle provided with a liquid chemical passage, and a connector for connection to a syringe, in which a fitting portion having claws and a needle are integrally molded by injection molding or the like (see, for example, Japanese Laid-Open Patent Publication No. 2005-516696 (PCT), Japanese Laid-Open Patent Publication No. 2005-504609 (PCT), and Japanese Laid-Open Patent Publication No. 2005-522282 (PCT)).

SUMMARY OF INVENTION

Meanwhile, as to vials in Japan, there is no unified standard, and such vials vary in shape and size among products of different makers. More specifically, the thickness of the rubber stopper and the height of the vial head portion for holding the rubber stopper and the like are factors that differ on a vial-to-vial basis, and there are a plurality of outside diameter values for the vial head portion. Previous vial adapters, however, are not configured to be capable of coping with such a variety. When a conventional vial adapter is used, therefore, an impermissible amount of liquid chemical may be left in the vial for the following reasons.

For instance, the height of the head portion of the vials according to the specification of a vial head portion with an outside diameter of 20 mm, as most commonly distributed, ranges from 6.0 mm to 8.0 mm, with a variance of about 2 mm. Generally, the position of a needle hole (a side hole provided in the needle) in a vial adapter is set in conformity with a vial which is the highest in terms of the height of the vial head portion. When such a vial adapter is used for a vial having a lower head portion height, therefore, the position of the needle hole of the vial adapter connected to the vial is located deeper inside the vial than necessary. In other words, the needle hole is located farther from the position of the back surface of the rubber stopper of the vial, resulting in a larger amount of liquid chemical being left in the vial. To cope with this situation, the person that prepares the drug may perform an operation of shifting the vial relative to the vial adapter in a direction to bring the needle hole closer to the back surface of the rubber stopper, within a range of chattering, but which is extremely poor in terms of operability.

In addition, since the thickness of rubber stoppers also varies on the basis of each rubber stopper, it is a common practice to set the position of the needle hole in the vial adapter in accordance with a thick rubber stopper. When the vial adapter is connected to a vial that is fitted with a thin rubber stopper, therefore, the position of the needle hole becomes located deeper inside the vial than necessary. Similar to the aforementioned case, this results in a larger amount of liquid chemical being left in the vial.

On the other hand, the number of expensive drugs, such as molecular target therapeutic agents, has been increasing in recent years. To avoid wasting such a drug, therefore, it is desirable for the liquid chemical in a vial to be recovered into a syringe or the like as completely as possible.

In methods of recovering a liquid chemical from a vial according to the related art, however, complicated work is needed in fitting a vial adapter to the vial as well as for recovering the liquid chemical into a syringe through a metallic needle or the like, which is provided with a liquid chemical passage therein.

More specifically, after the vial adapter has been attached to the vial, an outlet portion of a liquid chemical passage provided at a needle tip of a metallic needle or the like of the vial adapter is located outside the liquid surface of the liquid chemical, so that the outlet portion of the liquid chemical passage becomes exposed to a residual air region inside the vial. In a condition in which the outlet portion of the liquid chemical passage is exposed to the residual air region, air in the syringe is sent through the liquid chemical passage into the vial, to thereby establish a compressed state inside the vial. In this state, the outlet portion of the liquid chemical passage is located within the liquid chemical, whereby the liquid chemical is recovered into the syringe.

Use of the aforementioned method has been pointed out to produce a problem in that, in the case of a drug such as a carcinostatic agent or the like, which contains a protein carcinostatic agent or a surfactant, bubbling occurs during suction of the drug, thus making it impossible to perform accurate metering of the liquid chemical. Also, it is difficult to recover the chemical liquid in a non-wasteful manner. Further, the liquid chemical recovering operation is troublesome.

The present invention has been made in consideration of the above-mentioned circumstances. Accordingly, it is a first object of the present invention to provide a vial adapter, which ensures that when the vial adapter is connected to a vial, the position of a needle hole inside the vial can be located appropriately, whereby the amount of liquid chemical left inside the vial can be reduced substantially to zero.

Further, it is a second object of the present invention to provide a vial adapter, which ensures that when the vial adapter is connected to a vial, the position of the needle hole as a liquid chemical outlet portion inside the vial can be located appropriately, whereby the liquid chemical inside the vial can be recovered in a manner such that bubbling can be restrained from occurring.

In order to attain the aforementioned first object, according to the present invention, there is provided a vial adapter including a fitting portion, which has a flexible arm portion provided with a claw for engagement with a head portion of a vial and which can be fitted onto the head portion of the vial, and a hollow needle, which is disposed inside the fitting portion coaxially with the fitting portion, and which, when the fitting portion is fitted onto the head portion of the vial, pierces a stopper formed of an elastic material and that is mounted to the vial, the needle having a side hole near a distal end portion thereof, wherein the needle is provided at a proximal end portion thereof with a stopper contact portion, which abuts on a top surface of the stopper when the fitting portion is fitted onto the head portion of the vial. Also, when the fitting portion is fitted onto the head portion of the vial, the stopper contact portion abuts on the top surface of the stopper and the claw engages with the head portion of the vial, whereby the fitting portion is fixed to the head portion of the vial, and a region of the side hole nearest the proximal end of the needle is positioned either roughly at a back surface of the stopper or inside of the stopper.

According to the present invention, as noted above, the distance between the stopper contact portion and the claws of the fitting portion is set to be not more than the minimum of the variance in values anticipated as to the height of the vial head portion, whereby the position of the side hole (needle hole) relative to the back surface of the stopper is not influenced by the difference in the height of the head portion of the vial to which the fitting portion is connected. In addition, the distance from the region of the side hole nearest the proximal end to the stopper contact portion is set to be not more than the minimum of the variance in values anticipated as to the thickness of the stopper, whereby it is ensured, irrespective of variances in the stopper thickness, that the region of the side hole nearest the proximal end is located either roughly at the back surface of the stopper or inside of the stopper when the fitting portion is fitted onto the head portion of the vial. According to the vial adapter of the present invention, therefore, the influence of variances in the height of the head portion of the vial to be connected and the influence of variances in the stopper thickness can be suppressed, and the position of the side hole inside the vial upon connection of the vial adapter to the vial can be optimized. Consequently, the amount of liquid chemical left in the vial can be reduced substantially to zero.

In addition, the above-noted vial adapter may be characterized in that the needle is provided with a groove portion extending from the region of the side hole nearest the distal end of the needle toward a needle point of the needle.

According to the aforementioned configuration, even if the stopper is thick, the inside of the vial and the inside of the needle communicate with each other through the groove portion provided in the needle, so that the liquid chemical in the vial can be made to flow through the groove portion into the interior of the needle.

Further, the above-noted vial adapter may be characterized in that the fitting portion and the needle are configured as separate parts, wherein the fitting portion is formed of a material that is softer than a material constituting the needle.

According to the aforementioned configuration, for the material constituting the needle, a material having a sufficient hardness for piercing the stopper can be selected, whereas, for the material constituting the fitting portion, a material having flexibility adaptable to different vial head portion outside diameters can be selected. Therefore, the vial adapter can be adapted to vials of various outside diameters and shapes. As a result, resistance in fitting the fitting portion to a vial having a head portion with a large outside diameter is prevented from becoming excessively high. Moreover, even when the fitting portion is fitted onto a vial having a head portion with a small outside diameter, chattering can be prevented from occurring.

In addition, the above-noted vial adapter may be characterized in that the fitting portion is provided in a side portion thereof with a window into which part of an outer circumferential portion of the head portion of the vial is inserted when the fitting portion is fitted onto the head portion of the vial.

According to the aforementioned configuration, when the fitting portion is fitted onto the head portion of a vial, part of the head portion is inserted into the window. This ensures firmer fitting between the fitting portion and the head portion of the vial. Consequently, the vial cannot easily slip off.

Further, the above-noted vial adapter may be characterized by additionally including a hollow, tubular reduced-diameter adapter that can be mounted inside the fitting portion. A first reduced-diameter fitting portion, which is capable of being fitted onto a vial head portion having a first outside diameter smaller than a basic outside diameter with which the fitting portion can cope, is provided on one end side of the reduced-diameter adapter, and a first claw portion is provided on the inner circumferential side of the first reduced-diameter fitting portion. A second reduced-diameter fitting portion, which is capable of being fitted onto a vial head portion having a second outside diameter smaller than the first outside diameter, is provided on the other end side of the reduced-diameter adapter, and a second claw portion is provided on the inner circumferential side of the second reduced-diameter fitting portion. The vial adapter is provided therein with an adapter end insertion portion into which an end portion of the reduced-diameter adapter is inserted when the reduced-diameter adapter is mounted to the fitting portion. The reduced-diameter adapter can be mounted to the fitting portion in an orientation for enabling insertion of the first reduced-diameter fitting portion into the adapter end insertion portion, and can be mounted to the fitting portion in an orientation for enabling insertion of the second reduced-diameter fitting portion into the adapter end insertion portion.

According to the aforementioned configuration, the reduced-diameter adapter copes with the two head portion outside diameters, which are smaller than a basic head portion outside diameter. Therefore, by use of the reduced-diameter adapter, it is possible, using a single part, to cope with two additional vial head portion outside diameters. Consequently, it is possible to cope with three vial head portion outside diameters.

In addition, the above-noted vial adapter may be characterized in that the reduced-diameter adapter is provided on one end side thereof with a first engaging portion operative to engage with the claw when the reduced-diameter adapter is mounted to the fitting portion in an orientation for enabling insertion of the second reduced-diameter fitting portion into the adapter end insertion portion. Also, the reduced-diameter adapter is provided on the other end side thereof with a second engaging portion operative to engage with the claw when the reduced-diameter adapter is mounted to the fitting portion in an orientation for enabling insertion of the first reduced-diameter fitting portion into the adapter end insertion portion.

According to the aforementioned configuration, the reduced-diameter adapter is provided with the first engaging portion and the second engaging portion, which are capable of engaging with the claw provided on the fitting portion. This ensures that when the reduced-diameter adapter is mounted to the fitting portion, the claw of the fitting portion functions as a part for locking the reduced-diameter adapter. Therefore, it is possible, without complicating the configuration, to provide the fitting portion with a function of being fitted onto the vial, as well as a function of mounting the reduced-diameter thereon.

Further, the above-noted vial adapter may be characterized in that the distance from the first engaging portion of the reduced-diameter adapter to an end face of the other end of the reduced-diameter adapter, and the distance from the second engaging portion of the reduced-diameter adapter to an end face of the one end of the reduced-diameter adapter are slightly shorter than the distance from the claw to a deepest region of the adapter end insertion portion.

With the aforementioned configuration, vertical movement of the reduced-diameter adapter within the fitting portion is restricted. In addition, since the reduced-diameter adapter is mounted to the fitting portion with little play, the reduced-diameter adapter can be mounted to the fitting portion without difficulty in connection.

In addition, the above-noted vial adapter may be characterized in that the reduced-diameter adapter is provided, between the first claw portion and the second claw portion, with a partition wall formed with an opening portion, which is sized to permit insertion of the stopper contact portion therein, and which is smaller than the first outside diameter.

According to the aforementioned configuration, it is ensured that when the reduced-diameter adapter is connected to a vial, vertical movement of the head portion of the vial within the reduced-diameter adapter can be restricted by the partition wall. Consequently, the mounting operation to mount the reduced-diameter adapter, which is connected to the vial, to the fitting portion can be smoothly performed.

According to the vial adapter of the present invention, the position of the needle hole inside a vial upon connection to the vial can be optimized, whereby the amount of a liquid chemical left inside the vial can be reduced substantially to zero.

In order to attain the aforementioned second object, according to the present invention, there is provided a vial adapter connected to a vial and used for recovery of a drug present inside the vial, including a fitting portion, which has a flexible arm portion provided with a claw for engagement with a head portion of the vial, and which can be fitted onto the head portion of the vial, a pressure buffer portion, which is provided on a side surface of the vial adapter, and which has an expansion portion formed of a soft material, and a holding portion for holding the expansion portion, and a hollow needle, which is disposed inside the fitting portion coaxially with the fitting portion, and which, when the fitting portion is fitted onto the head portion of the vial, pierces a stopper formed of an elastic material and which is mounted to the vial. The needle includes a first side hole provided in a circumferential surface of the needle, a second side hole located near a distal end of the needle and provided in the circumferential surface on a distal end side relative to the first side hole, and a stopper contact portion provided at a proximal end portion of the needle and which is capable of abutting on the stopper. The vial adapter is provided therein with a first passage through which the first side hole and a connector communicate with each other, and a second passage through which the second side hole and the pressure buffer portion communicate with each other. When the fitting portion is fitted onto the head portion of the vial, the stopper contact portion abuts on the stopper and the claw engages with the head portion of the vial, whereby the fitting portion is fixed to the head portion of the vial, and the first side hole is positioned more on the inner side of the vial than the stopper.

According to the present invention, as mentioned above, the second side hole is located on the distal side of the needle in relation to the first side hole, and thus it is ensured that when the vial is inverted or turned upside down for suction of the liquid chemical from the vial, the second side hole can be located above the first side hole. As a result, at the time of sucking the liquid chemical into a syringe or the like, air in the expansion portion can be moved into the vial while preventing direct contact between the air and the liquid chemical. According to the aforementioned configuration, therefore, the liquid chemical can be recovered into the syringe without bubbling.

In addition, the above-noted vial adapter may be characterized in that the second side hole is provided on a circumferential surface of the needle farthest from the expansion portion.

According to the aforementioned configuration, it is ensured that at the time of sucking the liquid chemical present inside the vial, the process of positioning the second side hole in the region of air inside the vial can easily be confirmed. In other words, the expansion portion does not hamper the operation of visually confirming the second side hole.

In addition, the above-noted vial adapter may be characterized in that the first side hole and the second side hole are located such that an angle between a perpendicular from the center of the first side hole to the axis of the needle and a perpendicular from the center of the second side hole to the axis of the needle is in a range from 90 to 270 degrees in the visual field of a section orthogonal to the axis of the needle.

According to the aforementioned configuration, it is ensured that at the time of sucking a liquid chemical from the inside of a vial through the first side hole, the second side hole and the first side hole are prevented from being positioned in the same plane. Consequently, generation of bubbling is restrained, and the liquid chemical can be recovered in a non-wasteful manner.

Further, the above-noted vial adapter may be characterized in that the first passage is a liquid chemical passage primarily for injection or recovery of a liquid chemical.

In addition, the above-noted vial adapter may be characterized in that the second passage is an air passage primarily for moving air present inside the vial.

Further, the above-noted vial adapter may be characterized in that an identification portion for identification of the position of the second side hole is provided in the vicinity of the second side hole.

According to the aforementioned configurations, the position of the second side hole can easily be distinguished. This ensures that at the time of recovering a liquid chemical that is present inside the vial, the second side hole can easily be positioned above the liquid surface of the liquid chemical (i.e., be positioned within the layer of air) inside the vial.

DESCRIPTION OF EMBODIMENTS

First Embodiment

Figure 1:
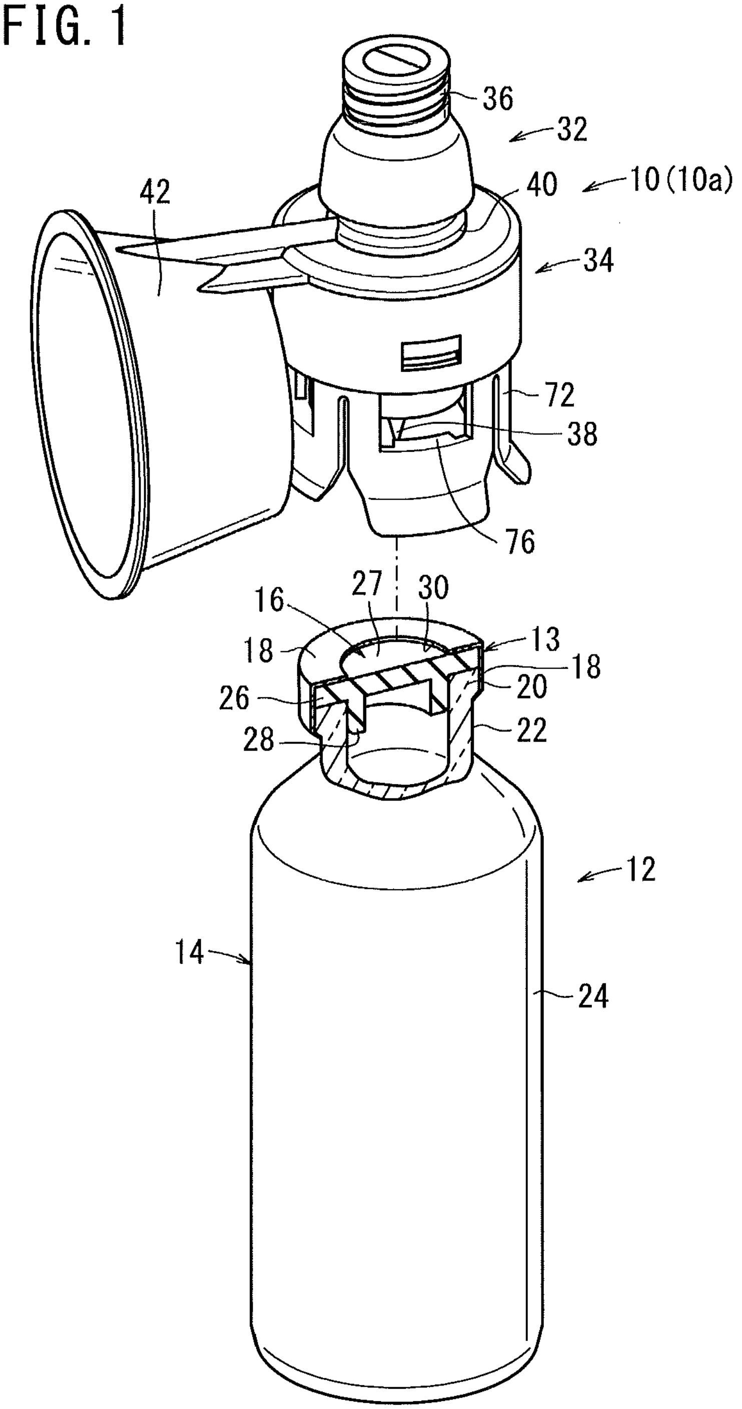
FIG. 1 is a perspective view of a vial adapter according to a first embodiment of the present invention, and a vial for connection thereto.

Next, a vial adapter according to the present invention will be described below, while showing preferred embodiments thereof with reference to the accompanying drawings. FIG. 1 is a perspective view showing a vial adapter 10 according to a first embodiment of the present invention, and a vial 12 for connection thereto.

First, the vial 12, as an object to which the vial adapter 10 is connected, will be described. The vial 12 contains a drug therein. The drug is a powdery or particulate solid or liquid. In the case that the drug is a powdery or particulate solid, the drug is dissolved in a dissolving liquid in order to prepare a liquid chemical, which thereafter is transferred from the vial 12 into a syringe 80 (see FIG. 6). If the drug is a liquid, the liquid is mixed with a diluting liquid (distilled water or the like) for dilution to a desired concentration, to thereby prepare a liquid chemical, which thereafter is transferred from the vial 12 into a syringe 80.

The vial 12 includes a hard container body 14, a stopper (rubber stopper) 16 formed of an elastic material and operative to seal a spout 20 of the container body 14 in an airtight manner, and a cap 18 that covers outer circumferences of the spout 20 of the container body 14 and the stopper 16. The container body 14 is formed, for example, from any of various glasses, various resins and the like, and has a light transmitting property (is substantially transparent or semi-transparent) for ensuring visibility of the interior thereof.

The container body 14 includes the spout 20 constituting an upper end portion thereof, a neck portion 22 provided under the spout 20, and a barrel 24 constituting a part ranging from a portion directly under the neck portion 22 to a lower end portion. The outside diameter of the neck portion 22 is smaller than the outside diameters of the spout 20 and the barrel 24.

The stopper 16 includes a main body portion 26 and a fitting projection 28. The main body portion 26 is a part that is circular disk-like in shape, having an outside diameter approximately equal to that of the spout 20, and which abuts on an upper surface of the spout 20. The fitting projection 28 is a part that is fitted into an inner circumferential portion of the spout 20 of the container body 14, and is formed, for example, in a hollow cylindrical shape projecting from a back surface of the main body portion 26.

The cap 18 is formed, for example, from a soft metal such as aluminum, with an opening 30 provided on an upper surface thereof. A top surface (upper surface) 27 of the stopper 16 is exposed through the opening 30. The cap 18 covers an outer circumferential surface of the stopper 16, an upper surface edge portion of the stopper 16, an outer circumferential surface of the spout 20, and a lower surface edge portion of the spout 20. A head portion 13 of the vial 12 makes up a part, which is composed of the spout 20 of the container body 14, the stopper 16, and the cap 18.

As shown in FIG. 1, the vial adapter 10 according to the present embodiment has a first element 32 (vial upper portion) including a needle 38, and a second element 34 (adapter lower portion) including a plurality of claws 76, which are capable of engagement with the head portion 13 of the vial 12. In the present embodiment, the first element 32 and the second element 34 are produced as separate parts, which then are coupled together to form a unitary body.

Figure 2:
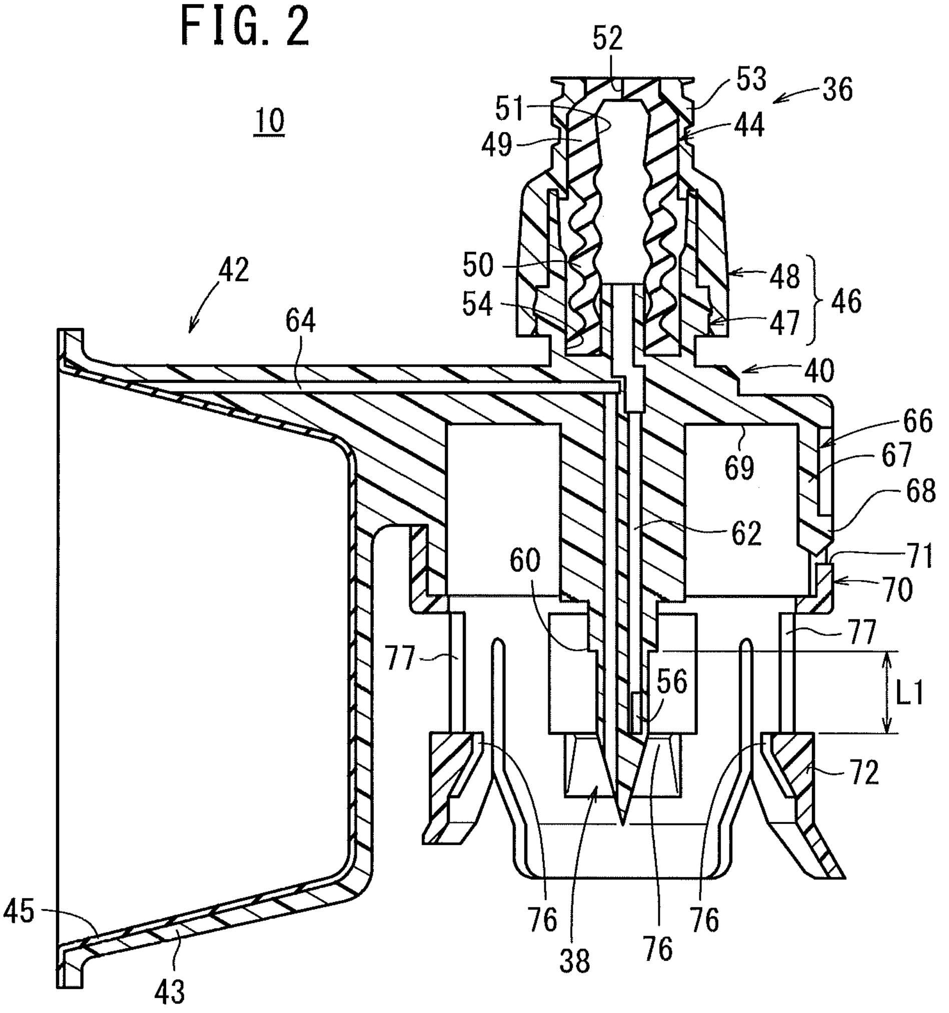
FIG. 2 is a longitudinal sectional view of the vial adapter.
Figure 3:
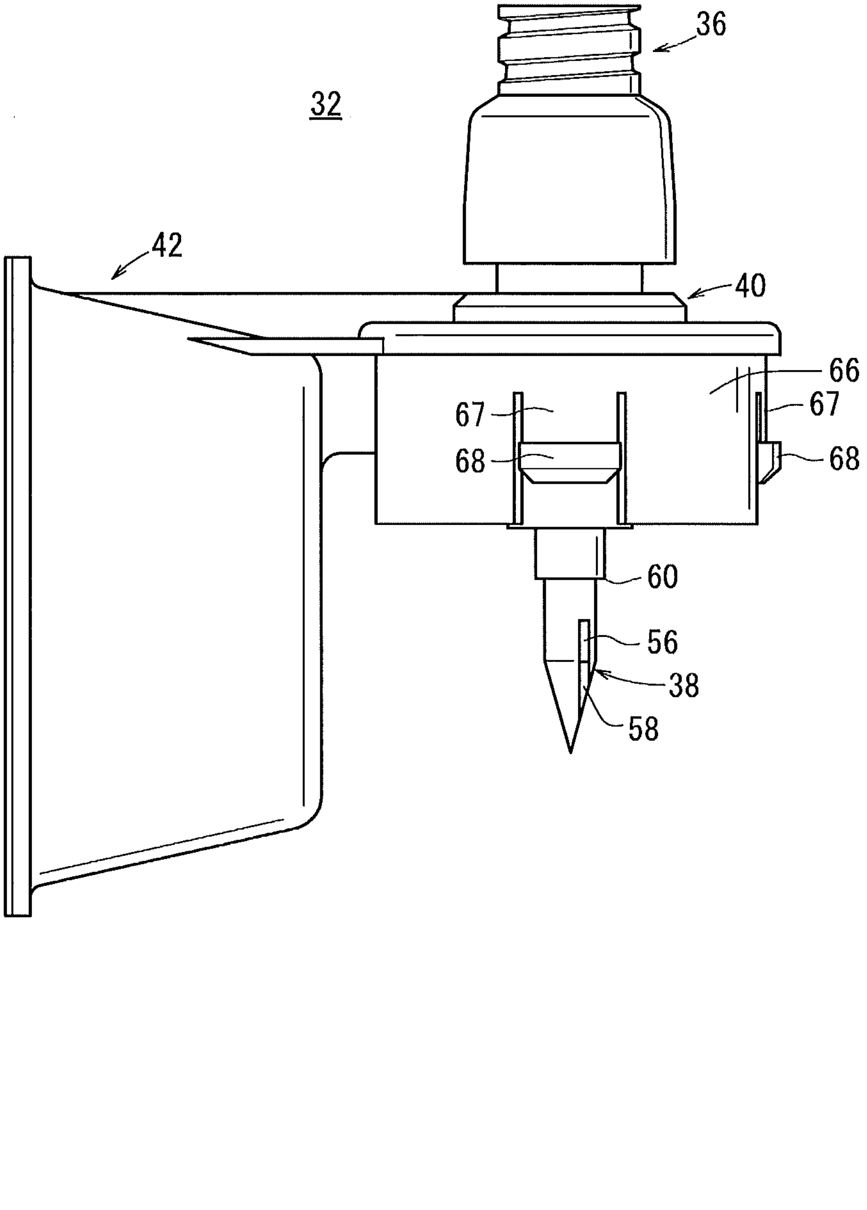
FIG. 3 is a side view showing a first element (upper adapter portion) of the vial adapter.

FIG. 2 is a longitudinal sectional view of the vial adapter 10, and FIG. 3 is a side view of the first element 32. A connector 36 for connection to the syringe 80 (see FIG. 6) is provided at one end portion (upper end portion) of the first element 32, while a needle 38 for puncturing the stopper 16 of the vial 12 is provided at the other end portion (lower end portion) of the first element 32. An intermediate portion 40 is provided between the connector 36 and the needle 38. In addition, in the first element 32, a pressure buffer portion (balloon portion) 42, which functions as a pressure compensation means, is provided on a lateral side of the intermediate portion 40.

As shown in FIG. 2, the connector 36 according to one exemplary configuration is provided with a valve body 44, which is roughly cylindrical in overall outside diameter shape, and a connector housing 46 in which the valve body 44 is contained (disposed).

The valve body 44 is formed of an elastic material (flexible material) capable of elastic deformation, and has a head portion 49, and a barrel portion 50 provided on the proximal end side of the head portion 49. The head portion 49 has an inner cavity 51 through which a liquid is capable of passing, and a slit 52, which extends from a planar top surface into the inner cavity 51. The barrel portion 50 is composed of a bellows-like tubular body. The barrel portion 50 functions as a deforming portion (biasing means), which biases the valve body 44 from the proximal end side toward the distal end side thereof.

The connector housing 46 comprises a housing body 47 and a cover portion 48. The housing body 47 is formed with an annular groove 54 therein. A proximal end portion of the aforementioned valve body 44 is inserted into the annular groove 54. The cover portion 48 is provided therein with a space containing the valve body 44, and is connected to a distal end portion of the housing body 47. A male screw portion 53 is formed on an outer circumference of the cover portion 48. The male screw portion 53 is capable of screw engagement with a female screw portion formed in a connection port 81 (see FIG. 6) provided at the distal end of the syringe 80.

The needle 38, which has a sharp needle point, is disposed in a fitting portion 72 coaxially with the fitting portion 72, and pierces the stopper 16 mounted to the vial 12 when the fitting portion 72 is fitted onto the head portion 13 of the vial 12. The needle 38 is formed with a side hole 56 in a location near a distal end portion thereof. The side hole 56 penetrates through the needle 38, between the inside and the outside of the needle 38. In addition, the needle 38 is provided with a groove portion 58, which extends from the region of the side hole 56 nearest the distal end portion toward the needle point of the needle 38.

Figure 4:
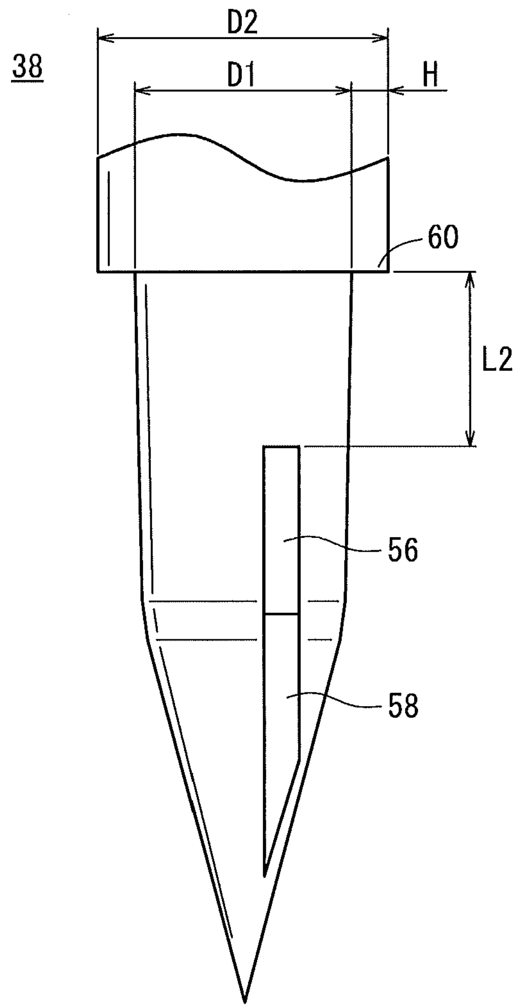
FIG. 4 is an enlarged side view showing a needle of the vial adapter.

The needle 38 is provided at a proximal end portion thereof with a stopper contact portion 60, which abuts on the top surface 27 of the stopper 16 when the fitting portion 72 is fitted onto the head portion 13 of the vial 12. FIG. 4 is an enlarged side view showing the distal end portion of the needle 38 and the vicinity thereof. The outside diameter D1 of a base end portion of the needle 38 is preferably set to from 1 to 4.5 mm, and more preferably, is set to from 2 to 4 mm. Further, the outside diameter D2 of the stopper contact portion 60 is preferably set to from 2 to 5 mm, and more preferably, is set to from 3 to 4.5 mm.

In addition, one half (½) of the difference between the outside diameter D2 of the stopper contact portion 60 and the outside diameter D1 of the base end portion of the needle 38, or the height H of a step formed by the stopper contact portion 60, preferably is set to be not less than 0.5 mm, and more preferably, is set to be not less than 1 mm. If the step height H is less than 0.5 mm, the stopper contact portion 60 would easily be urged into the stopper 16. On the other hand, the step height H must be set so that the stopper contact portion 60 does not contact the inner edge of the opening 30 formed in the cap 18.

Incidentally, the cross section of each of the stopper contact portion 60 and the needle 38 is not particularly restricted. For example, the cross sectional shape may be circular, elliptical, polygonal, or the like.

As shown in FIG. 2, a liquid chemical passage 62 as a first passage, and an air passage 64 as a second passage are formed in the interior of the needle 38 and the intermediate portion 40. The liquid chemical passage 62 is a hollow portion that extends in the axial direction, communicates with the side hole 56 in the needle 38 at one end portion (upper end portion) thereof, and communicates with the inside of the valve body 44 of the connector 36 at the other end portion (lower end portion) thereof. Therefore, the side hole 56 and the connector 36 communicate with each other through the liquid chemical passage 62. The air passage 64 opens at a distal end portion of the needle 38 at one end portion thereof, extends in the axial direction from the distal end portion of the needle 38 toward the connector 36, is bent at an intermediate portion 40 so as to extend toward the pressure buffer portion 42, and communicates with the interior of the pressure buffer portion 42 at the other end portion thereof. Therefore, the distal end portion of the needle 38 and the pressure buffer portion 42 communicate with each other through the air passage 64.

The intermediate portion 40 is provided, at one part thereof on the side of the needle 38, with a hollow cylindrical first connection end portion 66 for connection with the second element 34. The first connection end portion 66 is provided at the outer circumference thereof with a plurality of engaging pieces 67 arranged at intervals along the circumferential direction. Each of the engaging pieces 67 is flexible and can be displaced in the radial direction through elastic deformation. Each of the engaging pieces 67 is provided with a claw 68 on the outer circumferential side of a distal end portion thereof. In addition, an adapter end insertion portion 69 is formed on the inside of the first connection end portion 66. The adapter end insertion portion 69 is an annular groove opening on the lower side (needle 38 side).

The pressure buffer portion 42 has a balloon housing 43 formed in a bottomed and open shape, with an expansion portion (balloon film) 45 formed of a flexible material and operative to close the opening of the balloon housing 43. The inside of the balloon housing 43 communicates with the aforementioned air passage 64. The expansion portion 45 is capable of deformation in accordance with variations in pressure inside the pressure buffer portion 42. In an initial state, the expansion portion 45 is contained within the balloon housing 43.

In the present embodiment, the needle 38 makes up a member that is formed integrally with the intermediate portion 40 and the balloon housing 43. For the material constituting the member including the needle 38, a material is selected having a sufficient hardness for piercing the stopper 16. Examples of such materials include materials that are hard per se, such as polycarbonate, hard polyurethane, hard polypropylene, etc., as well as materials that are made harder by adding fillers or the like to general-use plastics.

Figure 5:
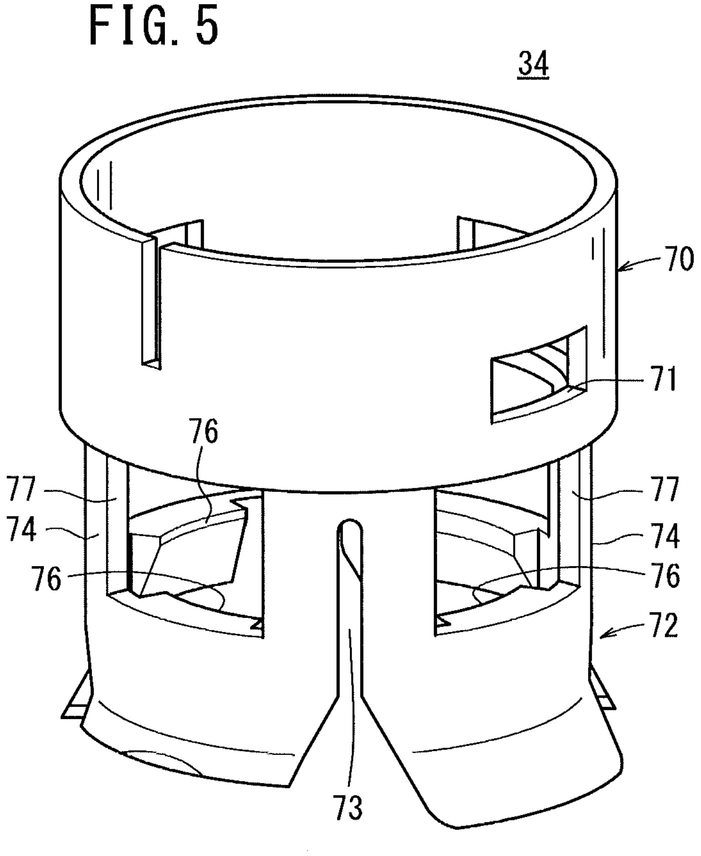
FIG. 5 is a side view showing a second element (lower adapter portion) of the vial adapter.

As shown in FIG. 5, the second element 34 is roughly cylindrical and hollow in overall shape. The second element 34 is provided on one end side (upper end portion side) thereof with a second connection end portion 70 for connection with the first connection end portion 66 of the first element 32, and further is provided on the other end portion side (lower end portion side) thereof with a fitting portion 72, which is capable of being fitted onto the head portion 13 of the vial 12.

For the material constituting the second element 34 including the fitting portion 72, a material is selected having flexibility so as to permit adaptation to different vial head portion outside diameters. Examples of suitable materials include polyacetal, polyurethane, and polyethylene.

The second connection end portion 70 makes up a part that is externally fitted onto the first connection end portion 66. The second connection end portion 70 is formed with a plurality of engaging opening portions 71, which penetrate through the inside and the outside thereof, at intervals along the circumferential direction. The claws 68, which are provided on the first connection end portion 66, engage with the engaging opening portions 71 provided in the second connection end portion 70, whereby the first connection end portion 66 and the second connection end portion 70 are connected together (see FIG. 2).

The fitting portion 72 includes a plurality of (in the illustrated example, four) flexible arm portions 74 arranged along the circumferential direction. Slits 73 that extend in the axial direction are provided respectively between the arm portions 74. On the inner circumferential side of each of the arm portions 74, a claw 76 (arm) for engagement with the head portion 13 of the vial 12 is provided. Between the claws 76 and the second connection end portion 70, a plurality of windows 77, which penetrate through the fitting portion 72 between the inside and the outside thereof, are formed at intervals along the circumferential direction. Each of the claws 76 constitutes one edge of the window 77.

As shown in FIG. 2, the distance L1 between the stopper contact portion 60 (the lower surface of the stopper contact portion 60) and the claws 76 (the upper surfaces of the claws 76) of the fitting portion 72 is set to be not more than the minimum of the variance in values anticipated as to the height of the head portion 13 of the vial 12. More specifically, the distance L1 is preferably set to be not more than 5.5 mm.

In addition, as shown in FIG. 4, the distance from the stopper contact portion 60 (the lower surface of the stopper contact portion 60) to the region of the side hole 56 most proximate to the proximal end side (the uppermost end position of the side hole 56) is set to be not more than the minimum of the variance in values anticipated as to the thickness of the stopper 16. More specifically, the distance L2 is set to be 1.0 to 4.0 mm, preferably 2.0 to 3.5 mm. If the distance L2 is less than 1.0 mm, leakage of the liquid chemical via the gap between the stopper 16 and the needle 38 is liable to occur. If the distance L2 exceeds 4.0 mm, the side hole 56 would become located at a deep position inside the vial 12 when the stopper of the vial 12 is punctured with the needle 38, thus resulting in an increase in the amount of liquid chemical left inside the vial 12.

The vial adapter 10 according to one embodiment of the present invention is basically constituted as described above. Next, operations and effects of the vial adapter 10 will be described below.

To prepare a liquid chemical by use of the vial adapter 10, first, the vial adapter 10 is connected to a vial 12. More specifically, the fitting portion 72 of the vial adapter 10 is placed on the head portion 13 of the vial 12, and the vial adapter 10 is pushed toward the vial 12 until the claws 76 provided on the fitting portion 72 of the vial adapter 10 reach the neck portion 22 and come into engagement with the head portion 13 of the vial 12.

Figure 6:
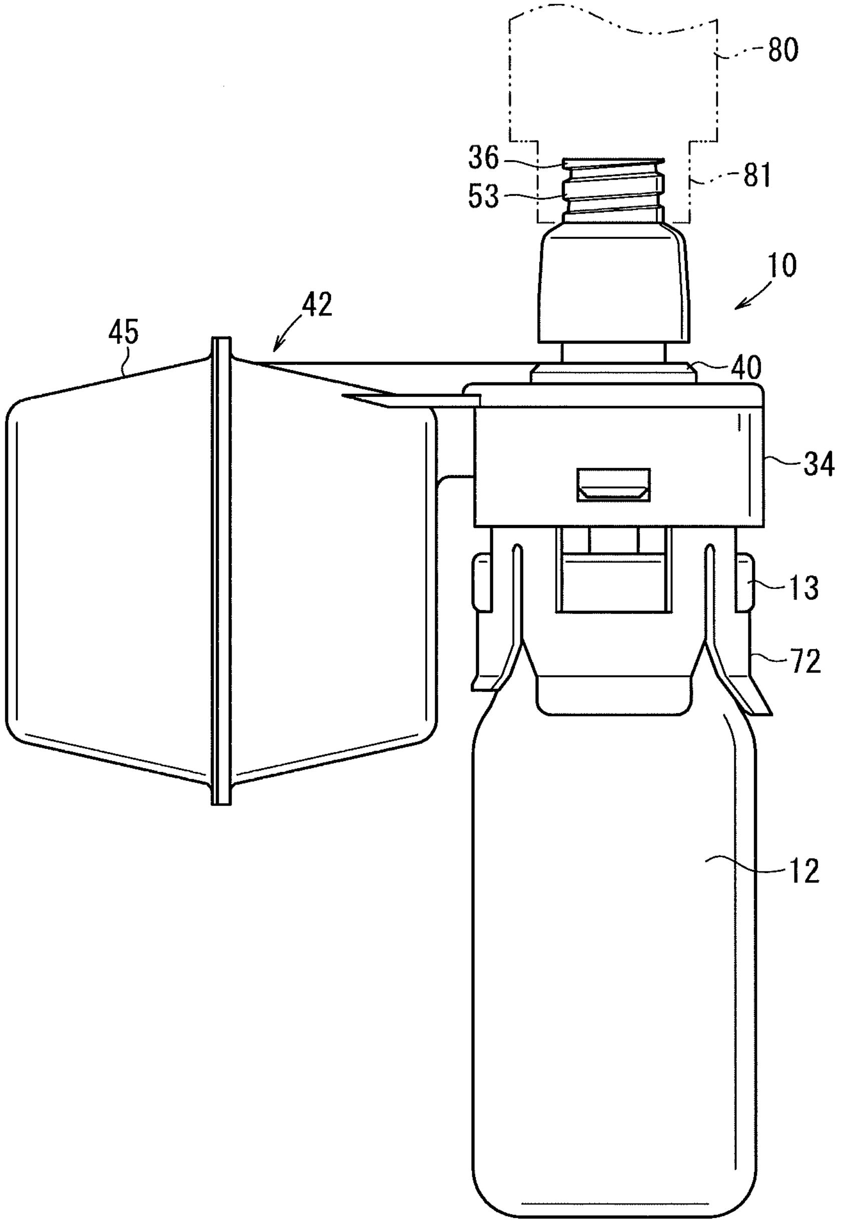
FIG. 6 is a side view showing a condition in which the vial adapter is connected to a vial.
Figure 7:
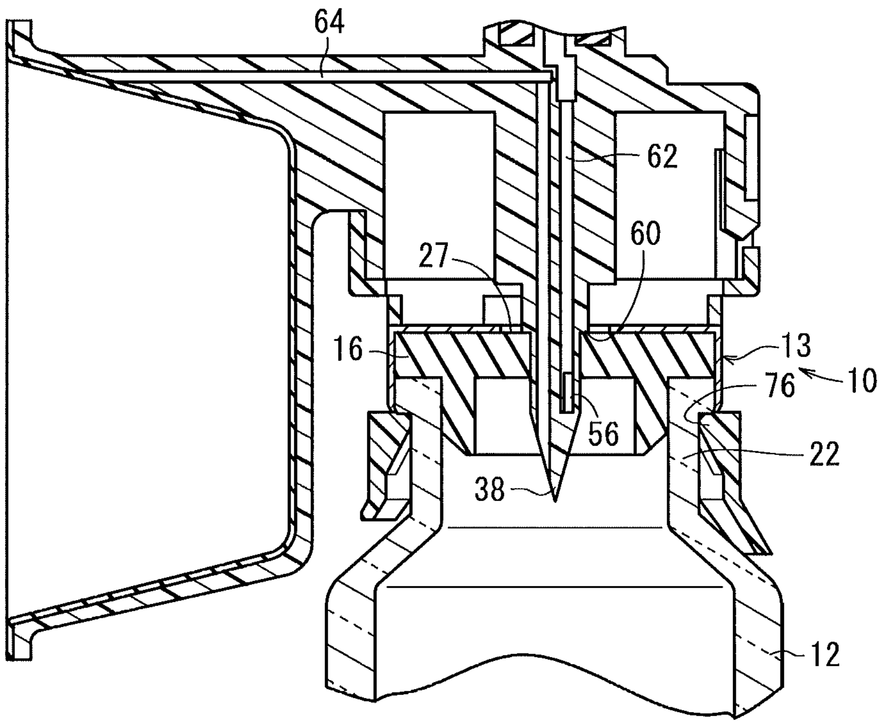
FIG. 7 is a partially omitted enlarged longitudinal sectional view showing the needle and the vicinity thereof when the vial adapter is connected to a vial having a head portion with a small height.

This results in connection of the vial adapter 10 to the vial 12, as shown in FIG. 6. In this instance, as shown in FIG. 7, the stopper contact portion 60 abuts on the top surface 27 of the stopper 16, and the claws 76 engage with the head portion 13 (i.e., the lower surface of the head portion 13) of the vial 12, whereby the fitting portion 72 becomes fixed to the head portion 13 of the vial 12. In this case, as mentioned above, the fitting portion 72 is provided in a side portion thereof with windows 77 into which parts of an outer circumferential portion of the head portion 13 of the vial 12 are inserted when the fitting portion 72 is fitted onto the head portion 13 of the vial 12. Therefore, the parts of the head portion 13 are inserted into the windows 77, whereby fitting between the fitting portion 72 and the head portion 13 of the vial 12 is fortified. Accordingly, the vial 12 will not easily slip off.

In addition, when the fitting portion 72 is fitted onto the head portion 13 of the vial 12, the needle 38 pierces the stopper 16 of the vial 12, and the side hole 56 is exposed to the inside of the vial 12. As a result, the liquid chemical passage 62 provided inside the vial adapter 10 and the inside of the vial 12 communicate with each other. In this instance, the region of the side hole 56 most proximate to the proximal end side is positioned either roughly at the same position as the back surface of the stopper 16, or inside of the stopper 16.

As mentioned above, the distance L1 (see FIG. 2) between the stopper contact portion 60 and the claws 76 of the fitting portion 72 is set to be not more than the minimum of the variance in values anticipated as to the height of the head portion 13 of the vial 12. Therefore, in the case of a vial 12 having a head portion 13 with a height approximately equal to the distance L1, namely, in the case of a vial 12 the head portion 13 of which is small in height, as shown in FIG. 7, fitting of the fitting portion 72 onto the head portion 13 of the vial 12 results in the stopper contact portion 60 coming into contact with the stopper 16 with a comparatively low contact surface pressure. In this case, the stopper 16 exhibits substantially no deformation toward the inside of the vial 12.

Figure 8:
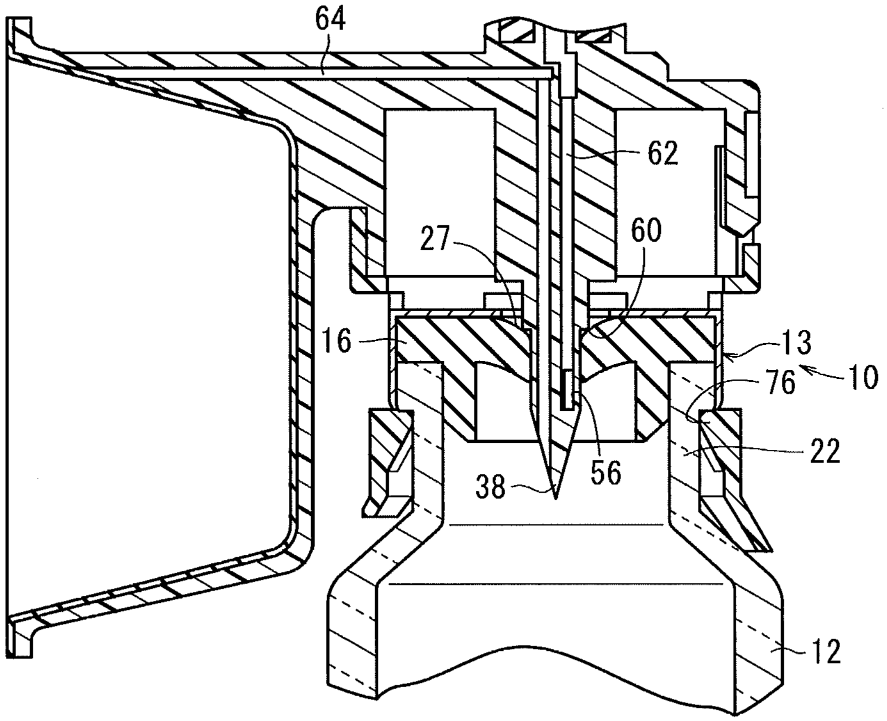
FIG. 8 is a partially omitted enlarged longitudinal sectional view showing the needle and the vicinity thereof when the vial adapter is connected to a vial having a head portion with a large height.

On the other hand, in the case that the height of the head portion 13 of a vial 12 is greater than the distance L1, namely, in the case of a vial 12 having a head portion 13 with a large height, as shown in FIG. 8, fitting of the fitting portion 72 onto the head portion 13 of the vial 12 results in the stopper contact portion 60 pressing the stopper 16 toward the inside of the vial 12, to thereby elastically deform the stopper 16. Accordingly, the position of the side hole 56 of the needle 38 relative to the back surface of the stopper 16 upon fitting of the fitting portion 72 onto the head portion 13 of the vial 12 is the same, irrespective of whether the height of the head portion 13 of the vial 12 is large or small. In other words, the position of the side hole 56 of the needle 38 relative to the back surface of the stopper 16 is not influenced by differences in the height of the head portion 13 of the connected vial 12.

Further, as mentioned above, the distance L2 (see FIG. 4) from the region of the side hole 56 most proximate to the proximal end side to the stopper contact portion 60 is set to be not more than the minimum of the variance in values anticipated as to the thickness of the stopper 16. Therefore, as shown in FIGS. 7 and 8, when the fitting portion 72 is fitted onto the head portion 13 of the vial 12, the region of the side hole 56 most proximate to the proximal end side is positioned either at roughly the same position as the back surface of the stopper 16, or inside of the stopper 16. In other words, even when there is a variance in the thickness of the stopper 16, the region of the side hole 56 most proximate to the proximal end side will not become positioned on a side of the inside of the vial 12 relative to the back surface of the stopper 16.

After the fitting portion 72 has been connected to the head portion 13 of the vial 12, the connection port 81 provided at the distal end portion of the syringe 80 is placed in screw engagement with the connector 36 of the vial adapter 10, as shown in FIG. 6, whereby the vial adapter 10 and the syringe 80 are connected to each other. In this instance, the valve body 44 (see FIG. 2) of the connector 36 is pressed by the distal end portion of the syringe 80 so as to be elastically deformed in the axial direction, whereby the slit 52 provided at the head portion 49 of the valve body 44 opens. As a result, the inside of the syringe 80 and the inside of the vial 12 communicate with each other through the liquid chemical passage 62 provided inside the vial adapter 10.

Next, a pusher (not shown) provided in the syringe 80 is pushed in, whereby a liquid (a dissolving liquid or a diluting liquid) in the syringe 80 is transferred into the vial 12 through the liquid chemical passage 62 in the vial adapter 10. In this instance, air that is present inside the vial 12 is moved, in an amount corresponding to the volume of the liquid introduced into the vial 12, through the air passage 64 and into the pressure buffer portion 42. As a result, the expansion portion 45 of the pressure buffer portion 42 becomes inflated, as shown in FIG. 6. This prevents the pressure inside the vial 12 from rising. In the case that the drug contained in the vial 12 is, for example, a carcinostatic agent, it is undesirable that a positive pressure is established in the vial 12. From this point of view, since the pressure inside the vial 12 is prevented from rising by the pressure buffer portion 42, mixing of the drug with the liquid can be performed safely.

After the drug has been dissolved in or diluted with the liquid transferred from the syringe 80 and the liquid chemical is thereby prepared, the vial 12 together with the vial adapter 10 is inverted or turned upside down, that is, a condition is established in which the vial 12 is located on the upper side and the vial adapter 10 is located on the lower side, and then the pusher in the syringe 80 is pulled. As a result, the liquid chemical in the vial 12 is moved into the syringe 80 through the liquid chemical passage 62 in the vial adapter 10. In this instance, the air in the pressure buffer portion 42 is moved into the vial 12 through the air passage 64, in an amount corresponding to the volume of the liquid chemical flowing out of the vial 12, so that the expansion portion 45 becomes deflated (the expansion portion 45 is displaced to the side of the balloon housing 43).

As mentioned above, upon fitting the fitting portion 72 onto the head portion 13 of the vial 12, the region of the side hole 56 most proximate to the proximal end side is positioned either at roughly the same position as the back surface of the stopper 16, or inside of the stopper 16. When the vial 12 is inverted or turned upside down, therefore, the liquid chemical in the vicinity of the back surface of the stopper 16 flows into the liquid chemical passage 62 via the side hole 56 positioned at the back surface of the stopper 16, so that the amount of liquid chemical left inside the vial 12 can be reduced almost to zero.

Thus, the vial adapter 10 according to the present embodiment is configured so that the influence of variances in the height of the head portion 13 of the vial 12 to be connected, and variances in the thickness of the stopper 16 of the vial 12 can be suppressed, whereby the position of the side hole 56 inside the vial 12 can be optimized. Accordingly, the liquid chemical in the vial 12 can be drawn into the syringe 80 while leaving only a miniscule amount of liquid chemical inside the vial 12. Thus, the amount of liquid chemical that is wasted can be reduced.

In addition, as mentioned above, the needle 38 is provided with the groove portion 58, which extends from the region of the side hole 56 most proximate to the distal end side to the needle point of the needle 38 (see FIG. 3). This ensures that, even in the case that the stopper 16 is thick, the inside of the vial 12 and the inside of the needle 38 can be placed in communication with each other through the groove portion 58 provided in the needle 38, so that the liquid chemical in the vial 12 can flow to the inside of the needle 38 through the groove portion 58.

Meanwhile, in the case of a vial with a vial head portion outside diameter specification of 20 mm, which is the most commonly distributed specification, the head portion outside diameter is 20.0 to 21.0 mm, with a variance of about 1 mm. In a vial adapter, in general, the needle should have a hardness sufficient for piercing various types of rubber stoppers, while the claws should be flexible, so as to permit application to various vial head portion outside diameters. In the vial adapters according to the related art, however, the needle and the claws (fitting portion) are made up of the same material, and since priority must be placed on the function of the needle, a material with a high hardness is selected as the material for the vial adapter, and consequently, the claws can be deformed only with difficulty.

More specifically, in the vial adapters according to the related art, the inside diameter of the fitting portion is set around a rough median value (rough mean value) of the variance in values of the vial head portion outside diameter. In the case where the vial head portion outside diameter is large, therefore, the force required for fitting the fitting portion onto the head portion may be so large that the person who prepares the drug cannot attach the fitting portion onto the head portion. On the other hand, when the vial head portion outside diameter is small, chattering may be so large that the vial can easily slip off from the vial adapter.

In order to cope with the aforementioned problems, in the vial adapter 10 according to the present embodiment, the fitting portion 72 and the needle 38 are configured as separate component parts, and the fitting portion 72 is formed of a material that is more flexible than the material constituting the needle 38. Therefore, as the material that constitutes the needle 38, a material having a sufficient hardness for piercing the stopper 16 can be selected. On the other hand, as the material that constitutes the fitting portion 72, a material having sufficient flexibility so as to permit adaptation to different vial head portion outside diameters can be selected, thereby being adaptable to vials that vary in outside diameter and shape. As a result, resistance in fitting the fitting portion onto a vial with a large head portion outside diameter can be prevented from becoming excessively high, and simultaneously therewith, generation of chattering upon fitting the fitting portion onto a vial with a small head portion outside diameter can be prevented.

Figure 9:
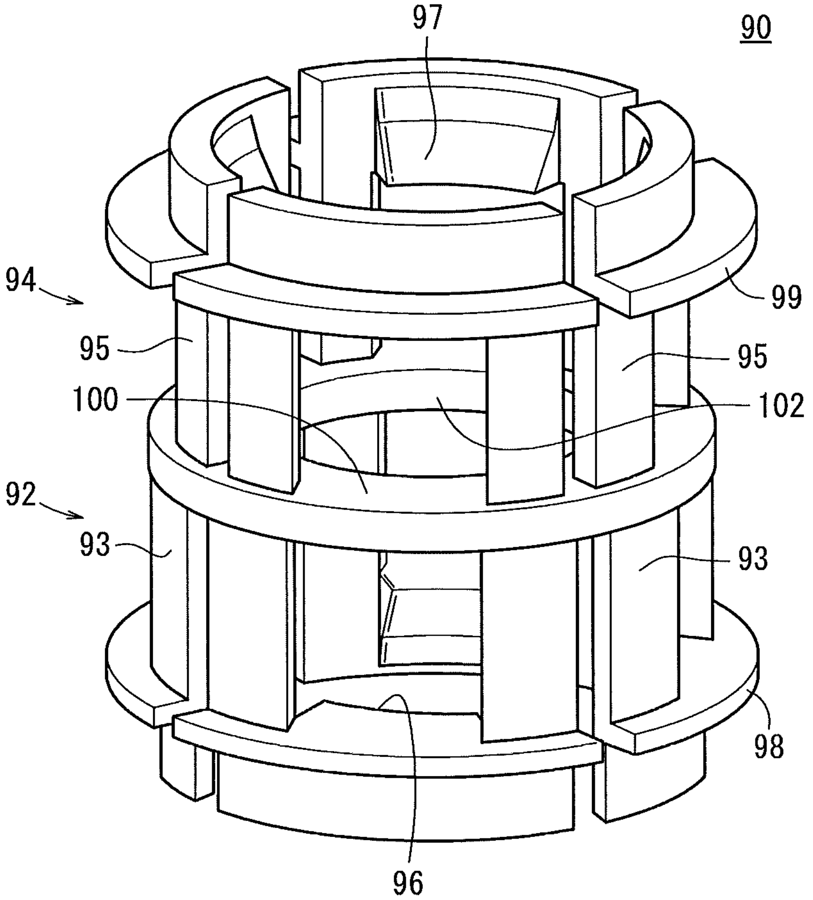
FIG. 9 is a general perspective view of an auxiliary adapter according to the first embodiment of the present invention.

Further, in the present invention, by additionally using a reduced-diameter adapter 90, as shown in FIG. 9, it is possible to cope with three vial head portion outside diameters. Hereinafter, the above-described vial adapter 10, which is composed of the first element 32 and the second element 34, will be referred to as the base adapter 10*a*, for distinguishing it from the reduced-diameter adapter 90.

The reduced-diameter adapter 90 is tubular and hollow in overall shape. The reduced-diameter adapter 90 can be mounted inside the fitting portion 72 of the base adapter 10*a*, and portions thereof on one end side and the other end side are configured so as to be capable of coping with adapter head portion outside diameters smaller than the adapter head portion outside diameters that can be coped with by the base adapter 10*a*.

More specifically, the reduced-diameter adapter 90 is provided on one end side thereof with a first reduced-diameter fitting portion 92 capable of being fitted onto a head portion of a vial having an outside diameter (hereinafter referred to as the first outside diameter) smaller than a basic outside diameter that the fitting portion 72 can cope with. The first reduced-diameter fitting portion 92 has a plurality of first arm portions 93 arrayed along the circumferential direction. Each of the first arm portions 93 is flexible, and can be elastically displaced in the radial direction. On the inner circumferential side of each of the first arm portions 93, a first claw portion 96 is provided, which can engage with the neck portion of a vial having a head portion of the first outside diameter.

In addition, the reduced-diameter adapter 90 is provided on the other end side thereof with a second reduced-diameter fitting portion 94, which can engage with the head portion of a vial having an outside diameter (hereinafter referred to as the second outside diameter) smaller than the first outside diameter. The second reduced-diameter fitting portion 94 has a plurality of second arm portions 95 arranged along the circumferential direction. Each of the second arm portions 95 is flexible, and can be elastically displaced in the radial direction. On the inner circumferential side of each of the second arm portions 95, there is provided a second claw portion 97, which can engage with the neck portion of a vial having a head portion of the second outside diameter. Examples of the material constituting the reduced-diameter adapter 90 include the same materials as those for the second element 34 described above.

Figure 10:
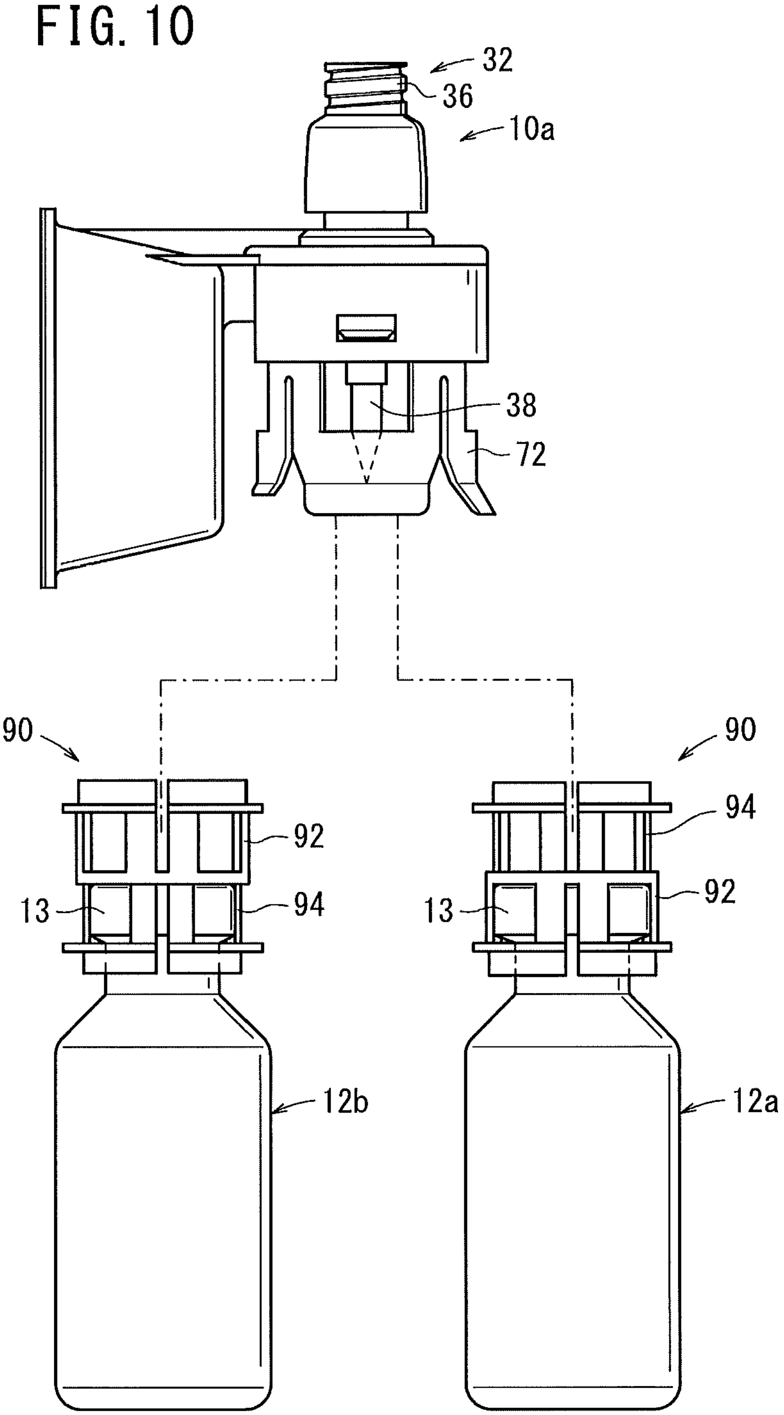
FIG. 10 is an illustration of a method of using the auxiliary adapter.

The reduced-diameter adapter 90 can be mounted to the fitting portion 72 in an orientation for enabling insertion of the first reduced-diameter fitting portion 92 into the adapter end insertion portion 69, and also can be mounted to the fitting portion 72 in an orientation for enabling insertion of the second reduced-diameter fitting portion 94 into the adapter end insertion portion 69. As shown in FIG. 10, therefore, the reduced-diameter adapter 90 can be mounted to the fitting portion of the base adapter 10*a*, both in the case where the first reduced-diameter fitting portion 92 is fitted onto the head portion 13 of a vial 12*a* with a first outside diameter (e.g., 15 mm) specification, and in the case where the second reduced-diameter fitting portion 94 is fitted onto the head portion 13 of a vial 12*b* with a second outside diameter (e.g., 13 mm) specification.

Accordingly, by mounting the reduced-diameter adapter 90 to the fitting portion 72, it is possible to cope with three kinds of outside diameters of vials 12. More specifically, in the case that the outside diameter of the vial 12 to which the fitting portion 72 can be adapted, for example, is 20 mm, the first reduced-diameter fitting portion 92 may be set so as to be capable of coping with a vial head portion outside diameter of, for example, 15 mm, whereas the second reduced-diameter fitting portion 94 may be set so as to be capable of coping with a vial head portion outside diameter of, for example, 13 mm. By use of such a reduced-diameter adapter 90, with a single component part, it is possible to cope with two further kinds of vial head portion outside diameters.

Figure 11:
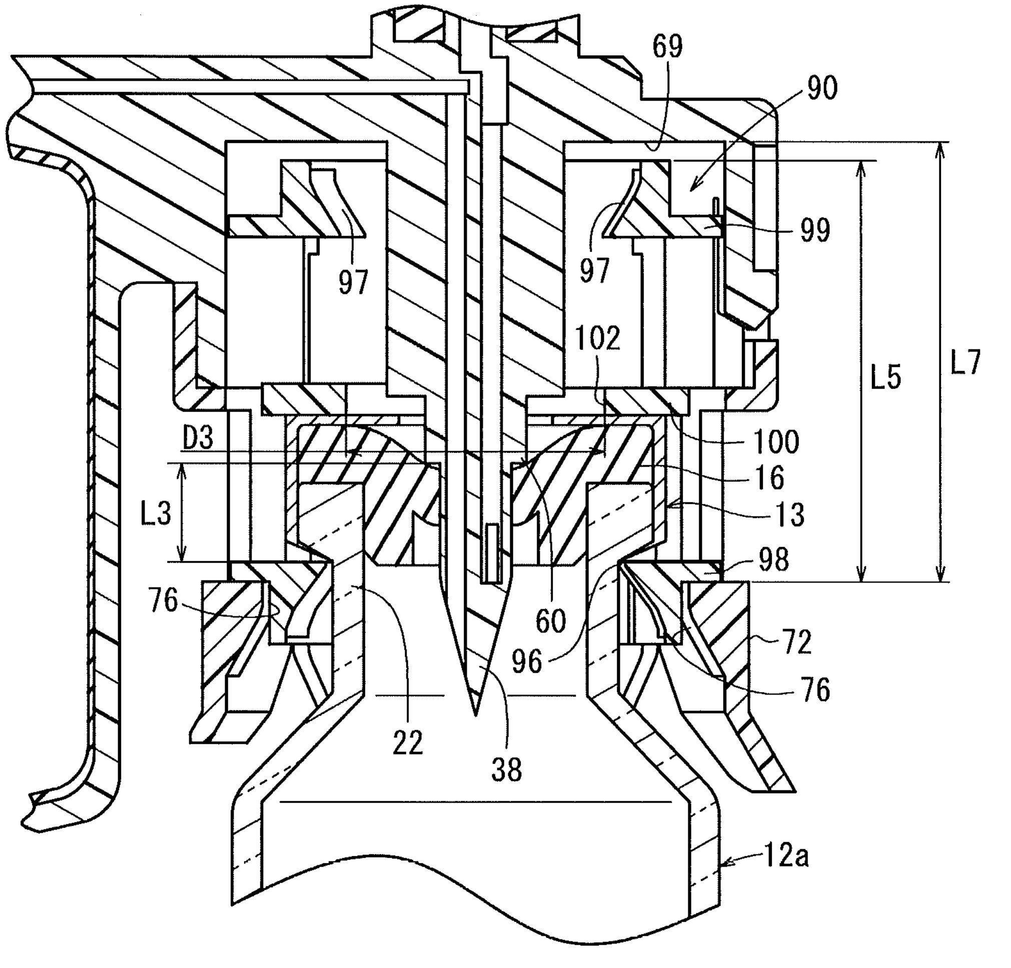
FIG. 11 is a partially omitted enlarged sectional view showing the needle and the vicinity thereof when a reduced-diameter adapter is mounted to a fitting portion in an orientation for enabling insertion of a second reduced-diameter fitting portion into an adapter end insertion portion.
Figure 12:
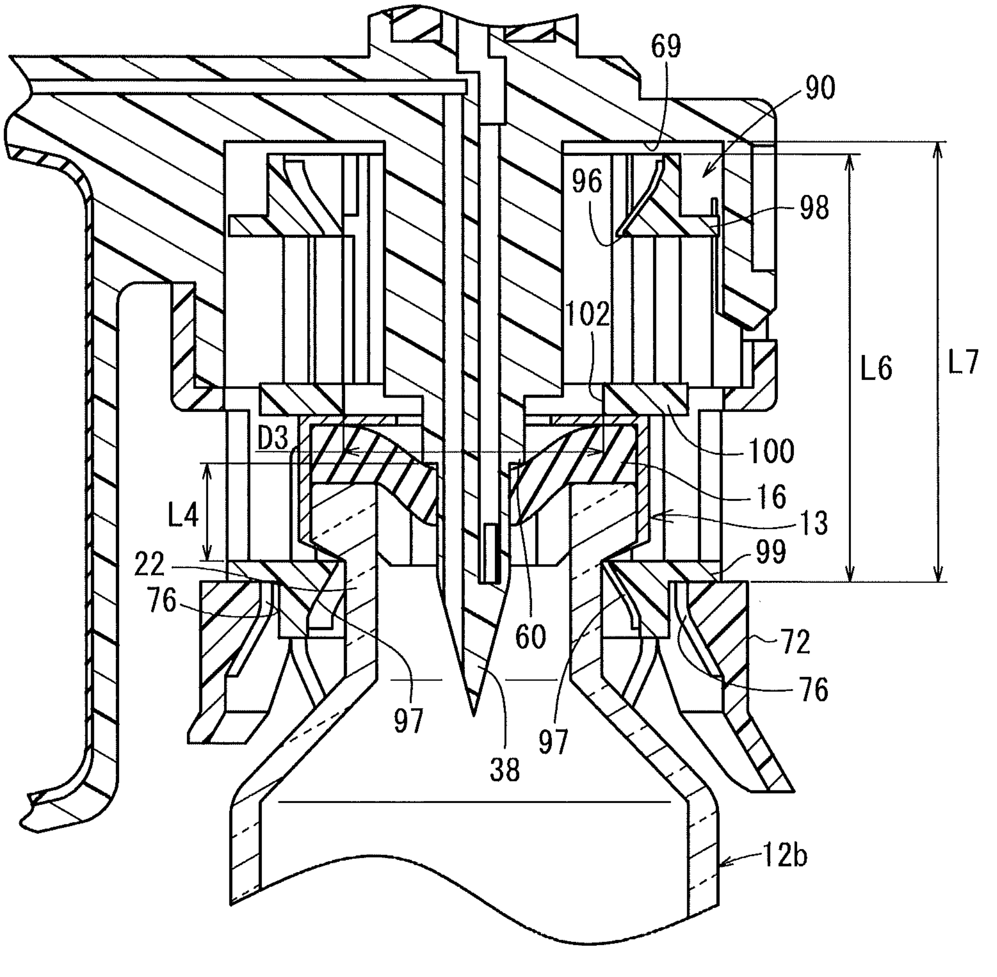
FIG. 12 is a partially omitted enlarged sectional view showing the needle and the vicinity thereof when the reduced-diameter adapter is mounted to the fitting portion in an orientation for enabling insertion of a first reduced-diameter fitting portion into the adapter end insertion portion.

FIG. 11 is a partially omitted enlarged sectional view showing the needle 38 and the vicinity thereof when the reduced-diameter adapter 90 is mounted to the fitting portion 72 in an orientation for enabling insertion of the second reduced-diameter fitting portion 94 into the adapter end insertion portion 69. In addition, FIG. 12 is a partially omitted enlarged sectional view showing the needle 38 and the vicinity thereof when the reduced-diameter adapter 90 is mounted to the fitting portion 72 in an orientation for enabling insertion of the first reduced-diameter fitting portion 92 into the adapter end insertion portion 69.

As shown in FIG. 11, the reduced-diameter adapter 90 is provided on one end side thereof with a first engaging portion 98, which engages with the claws 76 of the fitting portion 72 when the reduced-diameter adapter 90 is mounted to the fitting portion 72 in an orientation for enabling insertion of the second-reduced diameter fitting portion 94 into the adapter end insertion portion 69. Further, as shown in FIG. 12, the reduced-diameter adapter 90 is provided on the other end side thereof with a second engaging portion 99, which engages with the claws 76 of the fitting portion 72 when the reduced-diameter adapter 90 is mounted to the fitting portion 72 in an orientation for enabling insertion of the first reduced-diameter fitting portion 92 into the adapter end insertion portion 69.

Thus, the reduced-diameter adapter 90 is provided with the first engaging portion 98 and the second engaging portion 99, which can engage with the claws 76 provided on the fitting portion 72, whereby it is ensured that when the reduced-diameter adapter 90 is mounted to the fitting portion 72, the claws 76 of the fitting portion 72 function to lock the reduced-diameter adapter 90. More specifically, when the reduced-diameter adapter 90 is not used, the claws 76 of the fitting portion 72 function to lock the head portion 13 of the vial 12 having a basic outside diameter. On the other hand, when the reduced-diameter adapter 90 is used, the claws 76 function to lock the reduced-diameter adapter 90 so that the reduced-diameter adapter 90 will not slip off from the fitting portion 72. Since the claws 76 of the fitting portion 72 possess both of these two functions, it is possible, without complication of configuration, to provide the fitting portion 72 with a function to enable fitting thereof to a vial 12 having a head portion 13 of a basic outside diameter, as well as a function to enable mounting of the reduced-diameter adapter 90 thereto.

The distance L3 (see FIG. 11) from the first claw portions 96 to the stopper contact portion 60, when the reduced-diameter adapter 90 with the first reduced-diameter fitting portion 92 fitted onto the head portion 13 of the vial 12*a* is mounted to the fitting portion 72, similar to the distance L1, is set to be not more than the minimum of the variance in values anticipated as to the height of the head portion 13 of the vial 12*a*.

With the distance L3 set in the foregoing manner, it is ensured that when the reduced-diameter adapter 90 with the first reduced-diameter fitting portion 92 fitted onto the head portion 13 of a vial 12*a* is mounted to the fitting portion 72 of the base adapter 10*a*, as shown in FIG. 11, the stopper contact portion 60 abuts on the top surface 27 of the stopper 16, and the first claw portions 96 engage with the head portion 13 of the vial 12*a*. As a result, the head portion 13 of the vial 12*a* is fixed between the stopper contact portion 60 and the first claw portions 96. In addition, the region of the side hole 56 provided in the needle 38, which is located most proximate to the proximal end side, is positioned either at roughly the same position as the back surface of the stopper 16, or inside of the stopper 16.

Further, similar to the distance L1, the distance L4 (see FIG. 12) from the second claw portions 97 to the stopper contact portion 60 when the reduced-diameter adapter 90 with the second reduced-diameter fitting portion 94 fitted onto the head portion 13 of a vial 12*b* is mounted to the fitting portion 72 of the base adapter 10*a* is set to be not more than the minimum of the variance in values anticipated as to the height of the head portion 13 of the vial 12*b*.

With the distance L4 set in the foregoing manner, it is ensured that when the reduced-diameter adapter 90 with the second reduced-diameter fitting portion 94 fitted onto the head portion 13 of the vial 12*b* is mounted to the fitting portion 72 of the base adapter 10*a*, as shown in FIG. 12, the stopper contact portion 60 abuts on the top surface 27 of the stopper 16, and the second claw portions 97 engage with the head portion 13 of the vial 12*b*. Consequently, the head portion 13 of the vial 12 is fixed between the stopper contact portion 60 and the second claw portions 97. In addition, the region of the side hole 56 provided in the needle 38, which is located most proximate to the proximal end side, is positioned either at roughly the same position as the back surface of the stopper 16, or inside of the stopper 16.

As is clear from the foregoing, similar to the case of not using the reduced-diameter adapter 90, also in the case of using the reduced-diameter adapter 90, the amount of liquid chemical left inside the vial 12*a*, 12*b* can be reduced almost to zero.

As shown in FIG. 11, the distance L5 from the first engaging portion 98 to one end portion (i.e., the end portion on the side on which the second reduced-diameter fitting portion 94 is provided) of the reduced-diameter adapter 90 is set to be slightly shorter than the distance L7 from the claws 76 of the fitting portion 72 to the deepest portion of the adapter end insertion portion 69. In addition, as shown in FIG. 12, the distance L6 from the second engaging portion 99 to the other end portion (i.e., the end portion on the side on which the first reduced-diameter fitting portion 92 is provided) of the reduced-diameter adapter 90 is set to be slightly shorter than the distance L7 from the claws 76 of the fitting portion 72 to the deepest portion of the adapter end insertion portion 69. The difference between the distances L7 and L5, and the difference between the distance L7 and the distance L6, are preferably set to from 0.3 to 8 mm, and more preferably, are set to from 0.5 to 3 mm.

Since the distances L5 and L6 are set in the foregoing manner, vertical movement of the reduced-diameter adapter 90 within the fitting portion 72 is restricted. Further, since the reduced-diameter adapter 90 is mounted to the fitting portion 72 with little play, the connection in mounting the reduced-diameter adapter 90 to the fitting portion 72 can be prevented from becoming difficult to achieve.

In addition, as shown in FIG. 9, the reduced-diameter adapter 90 is provided, between the first claw portions 96 and the second claw portions 97, with a partition wall 100 formed with an opening portion 102, which is sized to permit insertion of the stopper contact portion 60 therein, and is smaller than the first outside diameter. More specifically, as shown in FIG. 12, the inside diameter D3 of the opening portion 102 in the partition wall 100 is set to be larger than the outside diameter D1 of the stopper contact portion 60, and to be smaller than the head portion outside diameter (second outside diameter) of the vial 12*b*. More specifically, the inside diameter D3 is preferably from 2 to 13 mm, and more preferably, from 6 to 10 mm. If the inside diameter D3 is smaller than 2 mm, the opening portion 102 (partition wall 100) and the stopper contact portion 60 may possibly come into contact with each other, which is undesirable.

Such a configuration ensures that when the reduced-diameter adapter 90 is connected to the vial 12*a*, 12*b* (see FIG. 10), vertical movement of the head portion 13 of the vial 12*a*, 12*b* within the reduced-diameter adapter 90 can be restricted by the partition wall 100. Consequently, the mounting operation upon connection of the reduced-diameter adapter 90 to the vial 12*a*, 12*b*, and mounting the reduced-diameter adapter 90 to the fitting portion 72 can be performed smoothly.

Incidentally, the outside diameter D2 (see FIG. 4) of the stopper contact portion 60 is set to be not greater than the inside diameter of the opening 30 in the cap 18 of the vial 12*b*, in order to ensure that when the fitting portion 72 is fitted onto the head portion 13 of the vial 12*b*, the stopper contact portion 60 directly contacts the stopper 16 of the vial 12*b* without coming into contact with the cap 18 of the vial 12*b*. Further, the outside diameter D2 of the stopper contact portion 60 is set to be greater than the outside diameter D1 of the base portion of the needle 38, in order to ensure that when the fitting portion 72 is fitted onto the head portion 13 of the vial 12, 12*a*, 12*b*, the stopper contact portion 60 comes into abutment on the top surface 27 of the stopper 16 assuredly. Specifically, the outside diameter D2 is preferably from 2.0 to 5.0 mm, and more preferably, from 3.0 to 4.5 mm.

Second Embodiment

Figure 13:
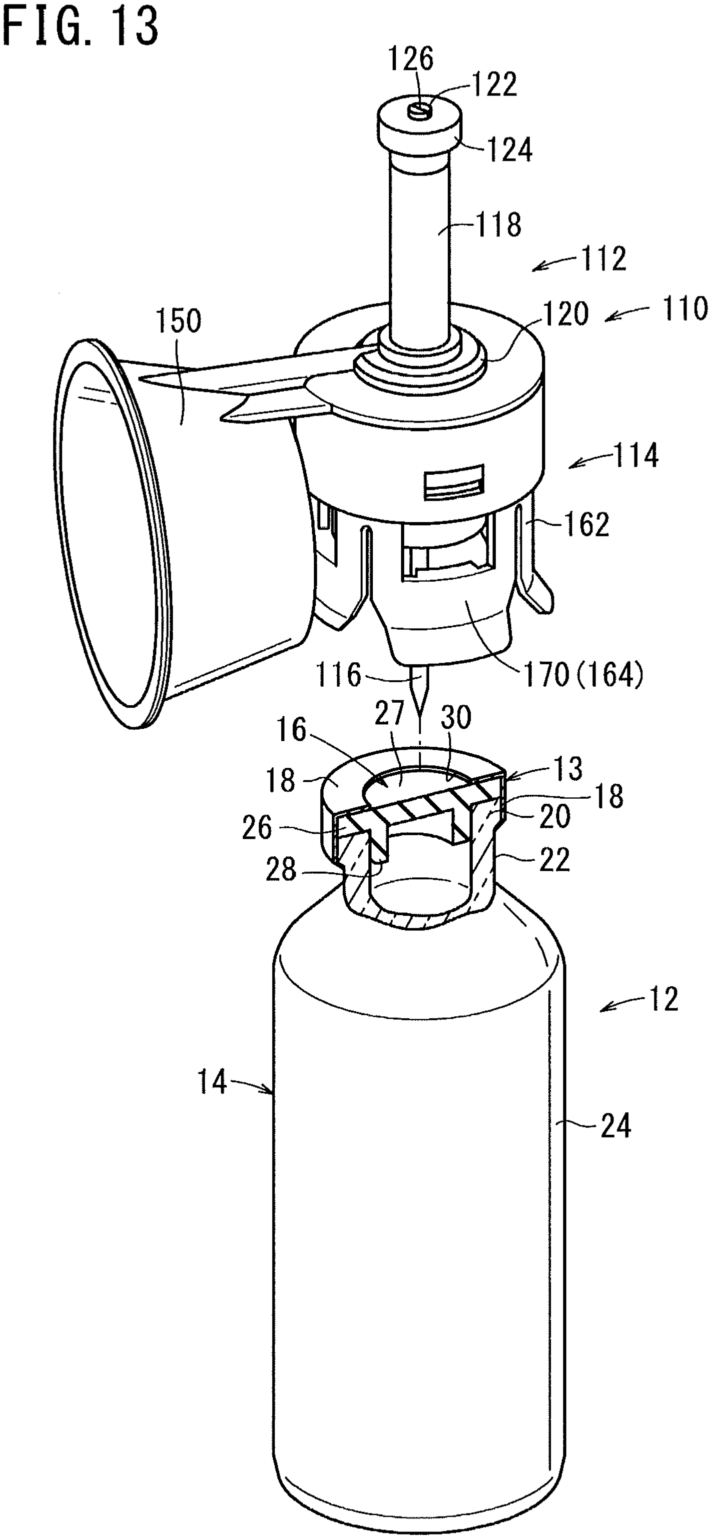
FIG. 13 is a perspective view of a vial adapter according to a second embodiment of the present invention, and a vial for connection thereto.

FIG. 13 is a perspective view showing a vial adapter 110 according to a second embodiment of the present invention, and a vial 12 to be connected thereto. Since the vial 12 is of the same configuration as the vial 12 shown in FIG. 12, detailed description thereof is omitted.

Figure 14:
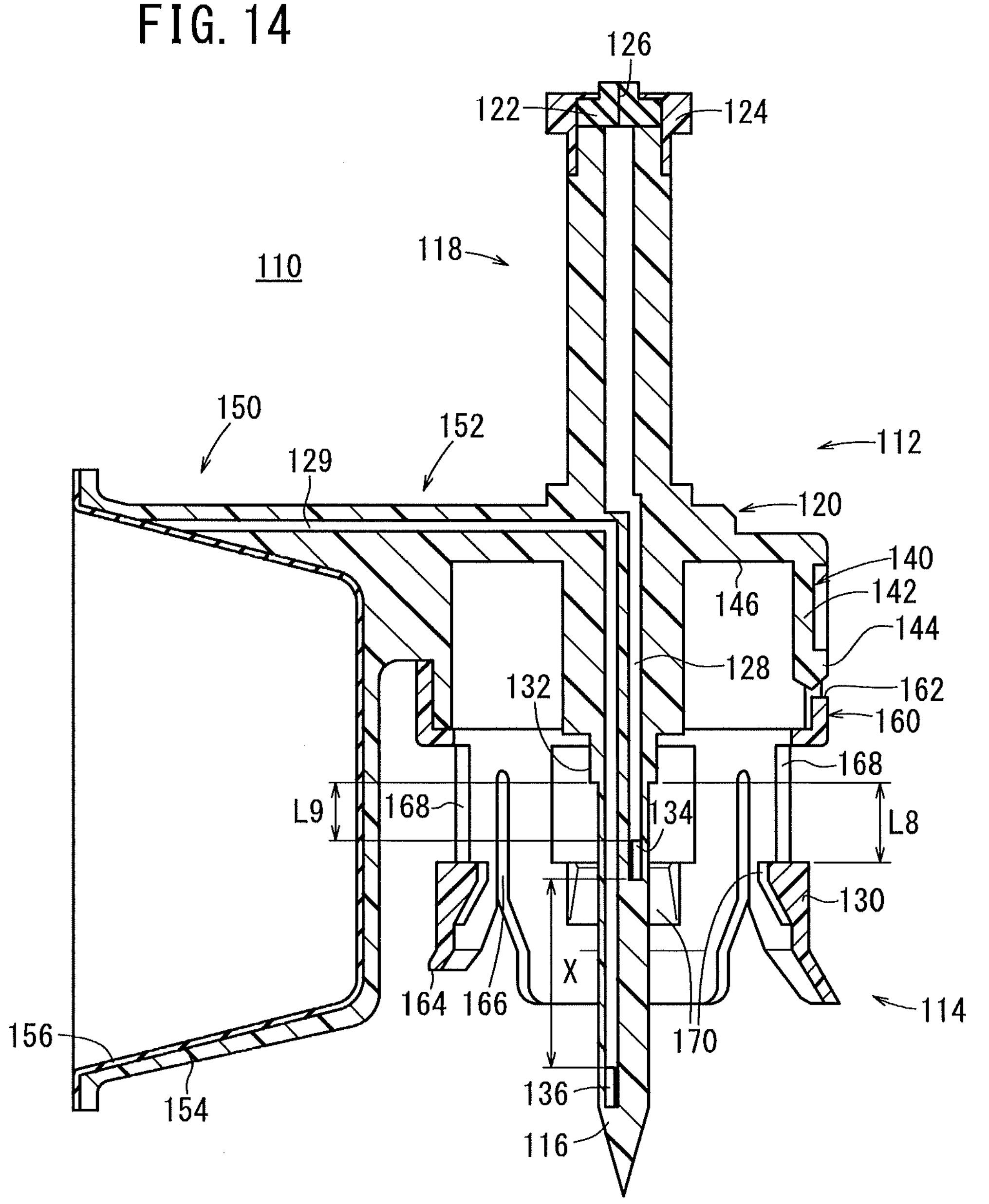
FIG. 14 is a longitudinal sectional view of the vial adapter according to the second embodiment of the present invention.
Figure 15:
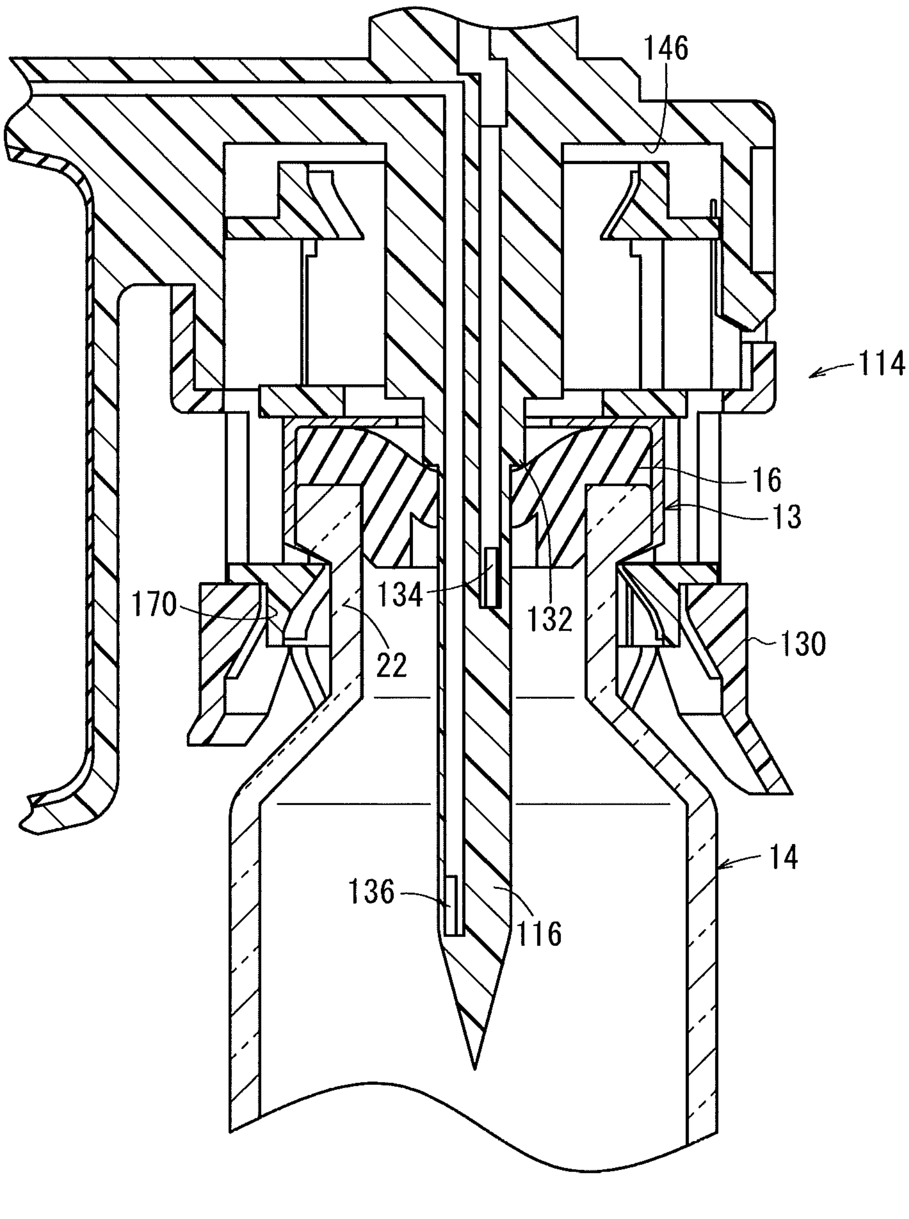
FIG. 15 is a side view of the vial adapter according to the second embodiment of the present invention, and a vial for connection thereto.

Referring to FIGS. 13 to 15, the vial adapter 110 according to the present embodiment will be described. The vial adapter 110 includes a first element 112 constituting an adapter upper portion, and a second element 114 constituting an adapter lower portion. The first element 112 and the second element 114 may be produced as separate component parts, which are coupled together to form a unitary body, or such elements may be molded together integrally.

FIG. 14 is a longitudinal sectional view of the vial adapter 110, and FIG. 15 is an enlarged side view showing a distal end portion of a needle 116 and the vicinity thereof. The first element 112 is provided at one end portion (upper end portion) thereof with a connector 118, which serves as a connection portion for connection to a syringe 80. The first element 112 is provided, continuously, at the other end portion (lower end portion) thereof with the needle 116, which is made to puncture a stopper 16 of the vial 12, and which projects to the interior of the second element 114. An intermediate portion 120 is provided between the connector 118 and the needle 116. In addition, in the first element 112, a pressure buffer portion 150, which functions as a pressure compensation means, is provided at a lateral side of the intermediate portion 120.

As shown in FIG. 14, the connector 118 according to one exemplary configuration of the connection portion includes a valve body 122, and a connector housing 124 in which the valve body 122 is contained (disposed).

The valve body 122 is roughly cylindrical in overall outside diameter shape, and is composed of an elastic member (flexible material) capable of elastic deformation. In addition, the valve body 122 may be provided with a slit 126 at a top surface thereof. In this case, the slit 126 is connected with a first passage 128, which will be described later.

The connector housing 124 holds the valve body 122 at an upper end portion of the connector 118, while covering the valve body 122 so that the top surface of the valve body 122 remains exposed. The connector housing 124 may be provided with screw engagement means, e.g., a screw, as a connection means for connection with the syringe 80, or may be provided with connection means in the form of an exclusive-use connector, which is capable of connection only with the connector housing 124.

The needle 116 is disposed inside a fitting portion 130 (described later) along the longitudinal direction of the vial adapter 110. The needle 116 has a sharp needle point and pierces the stopper 16 mounted to the vial 12 when the fitting portion 130 is fitted onto the head portion 13 of the vial 12. The needle 116, which has a hollow portion therein, is formed at a proximal end portion thereof with a stopper contact portion 132, and also is formed near the proximal end thereof with a first side hole 134, which will be described later. Further, the needle 116 is formed with a second side hole 136 on the distal end side relative to the first side hole 134 in the vicinity of the needle point. Each of the first side hole 134 and the second side hole 136 comprises a hole, which penetrates through the needle 116 from the outer surface to the hollow portion of the needle 116. In addition, the needle 116 may be provided with a groove (not shown) extending from a most distal end portion of the second side hole 136 toward the needle point of the needle 116.

The needle 116 is provided at a proximal end portion thereof with the stopper contact portion 132, which abuts on the top surface of the stopper 16 when the fitting portion 130 is fitted onto the head portion 13 of the vial 12. The outside diameter of a base portion of the needle 116 is preferably set to from 1 to 4.5 mm, and more preferably, is set to from 2 to 4 mm. Further, the outside diameter of the stopper contact portion 132 is preferably set to from 2 to 5 mm, and more preferably, is set to from 3 to 4.5 mm.

In addition, one half (½) of the difference between the outside diameter of the stopper contact portion 132 and the outside diameter of the base portion of the needle 116, or the height of a step formed by the stopper contact portion 132, is preferably set to be not less than 0.5 mm, and more preferably, is set to be not less than 1 mm. If the step height is less than 0.5 mm, the stopper contact portion 132 is liable to be urged into the stopper 16. On the other hand, the step height should be set such that the stopper contact portion 132 will not come into contact with the inner edge of the opening 30 formed in the cap 18.

Incidentally, the cross section of each of the stopper contact portion 132 and the needle 116 is not particularly restricted. For example, the cross sectional shape may be circular, elliptical, polygonal, or the like.

The needle 116 is provided with the first passage 128 and a second passage 129, each of which is in the form of a hollow portion. The first side hole 134 and the second side hole 136 are formed in the circumferential surface of the needle 116, and communicate with the first passage 128 and the second passage 129, respectively. The second side hole 136 is located on the side of the distal end of the needle 116 in relation to the first side hole 134. The distance X between the lower end of the first side hole 134 and the upper end of the second side hole 136 is preferably set to from 4 to 20 mm, and more preferably, is set to from 5 to 15 mm (see FIG. 14). Further, the first side hole 134 and the second side hole 136 are located such that the angle between a perpendicular from the center of the first side hole 134 to the axis of the needle 116 and a perpendicular from the center of the second side hole 136 to the axis of the needle 116 is in a range from 90 to 270 degrees, in the visual field of a section orthogonal to the axis of the needle 116.

The needle 116 and the intermediate portion 120 are formed therein with the first passage 128 and the second passage 129. The first passage 128 is a hollow portion that extends in the axial direction of the vial adapter 110, communicates at one end (lower end) thereof with the first side hole 134 in the needle 116, and communicates at the other end (upper end) thereof with the slit 126 in the valve body 122 of the connector 118. Therefore, the first side hole 134 and the connector 118 communicate with each other through the first passage 128. The second passage 129 communicates at one end thereof with the second side hole 136 in the needle 116, extends in the axial direction from the vicinity of the distal end of the needle 116 toward the side of the connector 118, is bent in an intermediate portion 120 to extend toward the side of the pressure buffer portion 150, and communicates at the other end thereof with the inside, of the pressure buffer portion 150. Therefore, the second side hole 136 in the vicinity of the distal end of the needle 116 and the pressure buffer portion 150 communicate with each other through the second passage 129.

The intermediate portion 120 is provided, in apart on the side of the needle 116, with a hollow cylindrical first connection end portion 140 for connection to the second element 114. The first connection end portion 140 is provided on the outer circumference thereof with a plurality of engaging pieces 142 arrayed at intervals along the circumferential direction. Each of the engaging pieces 142 is flexible, and can be displaced in the radial direction through elastic deformation. Each of the engaging pieces 142 is provided with an arm 144 on the outer circumferential side of a distal end portion thereof. In addition, the first connection end portion 140 is provided on the inside thereof with an adapter end insertion portion 146. The adapter end insertion portion 146 is an annular groove that opens on the lower side (the side of the needle 116).

The pressure buffer portion (balloon portion) 150 is provided on a lateral side of the intermediate portion 120, by way of an arm portion 152 therebetween. The pressure buffer portion 150 has a balloon housing 154 formed in a bottomed open shape, and an expansion portion formed of a flexible material and which is operative to close the opening portion of the balloon housing 154. The inside of the balloon housing 154 communicates with the second passage 129. The expansion portion 156 is capable of deformation in accordance with variations in pressure inside the pressure buffer portion 150. In an initial state, the expansion portion 156 is contained within the balloon housing 154, which serves as a holding portion.

In the present embodiment, the needle 116 is a member formed integrally with the intermediate portion 120 and the balloon housing 154. As the material constituting the member including the needle 116, a material having a sufficient hardness for piercing the stopper 16 is selected. Examples of suitable materials include materials that are hard per se, such as polycarbonate, hard polyurethane, hard polypropylene, etc., and materials which are made harder by adding fillers or the like to general-use plastics.

The second element 114 is roughly cylindrical and hollow in overall shape, is provided on one end side (upper end side) thereof with a second connection end portion 160 for connection to the first connection end portion 140 of the first element 112, and is provided on the other end side (lower end side) thereof with a fitting portion 130 capable of being fitted onto the head portion 13 of the vial 12.

As the material constituting the second element 114 including the fitting portion 130, a material having flexibility so as to permit adaptation to various vial head portion outside diameters is selected. Examples of such a material include polyacetal, polyurethane, and polyethylene.

The second connection end portion 160 forms a part that is externally fitted onto the first connection end portion 140. The second connection end portion 160 is formed with a plurality of engaging opening portions 162, which penetrate through the second connection end portion 160 between the inside and the outside thereof, at intervals along the circumferential direction. The arms 144 provided on the first connection end portion 140 engage with the engaging opening portions 162 provided in the second connection end portion 160, whereby the first connection end portion 140 and the second connection end portion 160 are connected together (see FIG. 14).

The fitting portion 130 has a plurality of flexible arm portions 164 arranged along the circumferential direction. Slits 166 extending in the axial direction are provided respectively between the arm portions 164. On the inner circumferential side of each of the arm portions 164, an arm (claw) 170 for engagement with the head portion 13 of the vial 12 is provided. Between the arms 170 and the second connection end portion 160, a plurality of windows 168 that penetrate through the fitting portion 72 between the inside and the outside thereof are formed at intervals along the circumferential direction. Each of the arms 170 constitutes one edge of the window 168.

The distance L8 between the stopper contact portion 132 (the lower surface of the stopper contact portion) and the arms 170 (the upper surfaces of the arms 170) of the fitting portion 130 is set to be not more than the minimum of the variance in values anticipated as to the height of the head portion 13 of the vial 12. More specifically, the distance L8 is preferably set to be not more than 5.5 mm.

In addition, the distance L9 from the stopper contact portion 132 (the lower surface of the stopper contact portion 132) to the region of the first side hole 134 most proximate to the proximal end side (the uppermost end position of the first side hole 134) is set to be not more than the minimum of the variance in values anticipated as to the thickness of the stopper 16. More specifically, the distance L9 is set to from 1.0 to 4.0 mm, and more preferably, from 2.0 to 3.5 mm. If the distance L9 is less than 1.0 mm, leakage of the liquid chemical via the gap between the stopper 16 and the needle 116 is liable to occur. If the distance L9 exceeds 4.0 mm, when the stopper 16 of the vial 12 is punctured with the needle 116, the first side hole 134 becomes located at a deep position inside the vial 12, resulting in an increase in the amount of liquid chemical left inside the vial 12.

Further, the distance from the stopper contact portion 132 (the lower surface of the stopper contact portion 132) to the region of the first side hole 134 most proximate to the proximal end side (the upper end position of the first side hole 134) is set to be not more than the minimum of the variance in values anticipated as to the vial. More specifically, the distance is set to from 2 to 5 mm, and more preferably, from 2.5 to 4.5 mm.

In addition, in the vicinity of the second side hole 136, an identification portion (not shown) is provided. The identification portion facilitates visual confirmation of the position of the second side hole 136 in the interior of the vial 12 when a liquid chemical is sucked from the vial 12. Examples of suitable identification portions include a marker and a rugged pattern.

The vial adapter 110 according to the second embodiment of the present invention is basically constituted as described above. Next, operations and effects of the vial adapter 110 will be described below.

To prepare a liquid chemical by use of the vial adapter 110, first, the vial adapter 110 is connected to a vial 12. More specifically, the fitting portion 130 of the vial adapter 110 is placed on the head portion 13 of the vial 12, and the vial adapter 110 is pushed toward the vial 12 until the arms 170 provided on the fitting portion 130 of the vial adapter 110 reach the neck portion 22 and come into engagement with the head portion 13 of the vial 12.

This results in the vial adapter 110 being connected to the vial 12. In this instance, as shown in FIG. 15, the stopper contact portion 132 abuts on the top surface of the stopper 16, and the arms 170 engage with the head portion 13 (more specifically, the lower surface of the head portion 13) of the vial 12, whereby the fitting portion 130 is fixed to the head portion 13 of the vial 12. In this case, as mentioned previously, the fitting portion 130 is provided in a side portion thereof with the windows 168, into which parts of an outer circumferential portion of the head portion 13 of the vial 12 are inserted when the fitting portion 130 is fitted onto the head portion 13 of the vial 12. Therefore, the parts of the head portion 13 enter into the windows 168, whereby the fitting between the fitting portion 130 and the head portion 13 of the vial 12 is fortified. Accordingly, the vial 12 cannot easily slip off.

In addition, when the fitting portion 130 is fitted onto the head portion 13 of the vial 12, the needle 116 pierces the stopper 16 of the vial 12, and the first side hole 134 becomes exposed to the inside of the vial 12. As a result, the first passage 128 provided inside the vial adapter 110 and the inside of the vial 12 communicate with each other. In this instance, the region of the first side hole 134 most proximate to the proximal end side is positioned either roughly at the same position as the back surface of the stopper 16, or inside of the stopper 16. In other words, the region of the first side hole 134 most proximate to the base end side is positioned in the vicinity of the stopper 16.

As described above, the distance L8 (see FIG. 14) between the stopper contact portion 132 and the arms 170 of the fitting portion 130 is set to be not more than the minimum of the variance in values anticipated as to the height of the head portion 13 of the vial 12. Therefore, in the case of a vial 12 having a head portion 13 with a height approximately equal to the distance L8, namely, in the case of a vial 12 the head portion 13 of which is small in height, fitting of the fitting portion 130 onto the head portion 13 of the vial 12 results in the stopper contact portion 132 coming into contact with the stopper 16 at a comparatively low contact surface pressure. In this case, the stopper 16 exhibits substantially no deformation toward the inside of the vial 12.

On the other hand, in the case that the height of the head portion 13 of the vial 12 is greater than the distance L8, namely, in the case of a vial 12 having a head portion 13 that is large in height, fitting of the fitting portion 130 onto the head portion 13 of the vial 12 results in the stopper contact portion 132 pressing the stopper 16 toward the inside of the vial 12, thereby elastically deforming the stopper 16. Accordingly, upon fitting of the fitting portion 130 onto the head portion 13 of the vial 12, the position of the first side hole 134 of the needle 116 relative to the back surface of the stopper 16 is the same, irrespective of whether the height of the head portion 13 of the vial 12 is large or small. In other words, the position of the first side hole 134 of the needle 116 relative to the back surface of the stopper 16 is not influenced by differences in the height of the head portion 13 of the connected vial 12.

In addition, as mentioned above, the distance L9 from the region of the first side hole 134 most proximate to the proximal end side to the stopper contact portion 132 is set to be not more than the minimum of the variance in values anticipated as to the thickness of the stopper 16. Therefore, when the fitting portion 130 is fitted onto the head portion 13 of the vial 12, the region of the first side hole 134 most proximate to the proximal end side is positioned either at roughly the same position as the back surface of the stopper 16, or inside of the stopper 16. In other words, even when variances as to the thickness of the stopper 16 occur, the region of the first side hole 134 most proximate to the proximal end side will not be positioned on the inside of the vial 12 relative to the back surface of the stopper 16.

After the fitting portion 130 has been connected to the head portion 13 of the vial 12, the connection port 81 (see FIG. 6) provided at the distal end portion of the syringe 80 is connected to the connector 118 of the vial adapter 110, whereby the vial adapter 110 and the syringe 80 are connected to each other. In this instance, the valve body 122 of the connector 118 is deformed by the distal end portion of the syringe 80, whereby the slit 126 provided at the top surface of the valve body 122 opens. In addition, the syringe 80 and the connector 118 may be connected to each other after a needle body or the like has been attached to the connection port. In that case, the valve body 122 is punctured with the needle body. As a result, the inside of the syringe 80 and the inside of the vial 12 are placed in communication with each other through the first passage 128 provided inside the vial adapter 110.

Next, a pusher (not shown) provided in the syringe 80 is pushed in, whereby a liquid (a dissolving liquid or a diluting liquid) in the syringe 80 is transferred into the vial 12 through the first passage 128 in the vial adapter 110. In this instance, air present inside the vial 12 is moved, in an amount corresponding to the volume of the liquid introduced into the vial 12, through the second passage 129 and into the pressure buffer portion 150. As a result, the expansion portion 156 of the pressure buffer portion 150 is inflated. This prevents the pressure inside the vial 12 from rising. In the case that the drug contained in the vial 12, for example, is a carcinostatic agent, it is undesirable for a positive pressure to be established in the vial 12. From this point of view, since the pressure inside the vial 12 is prevented from rising by the pressure buffer portion 150, mixing of the drug with the liquid can be performed safely.

Figure 16A:
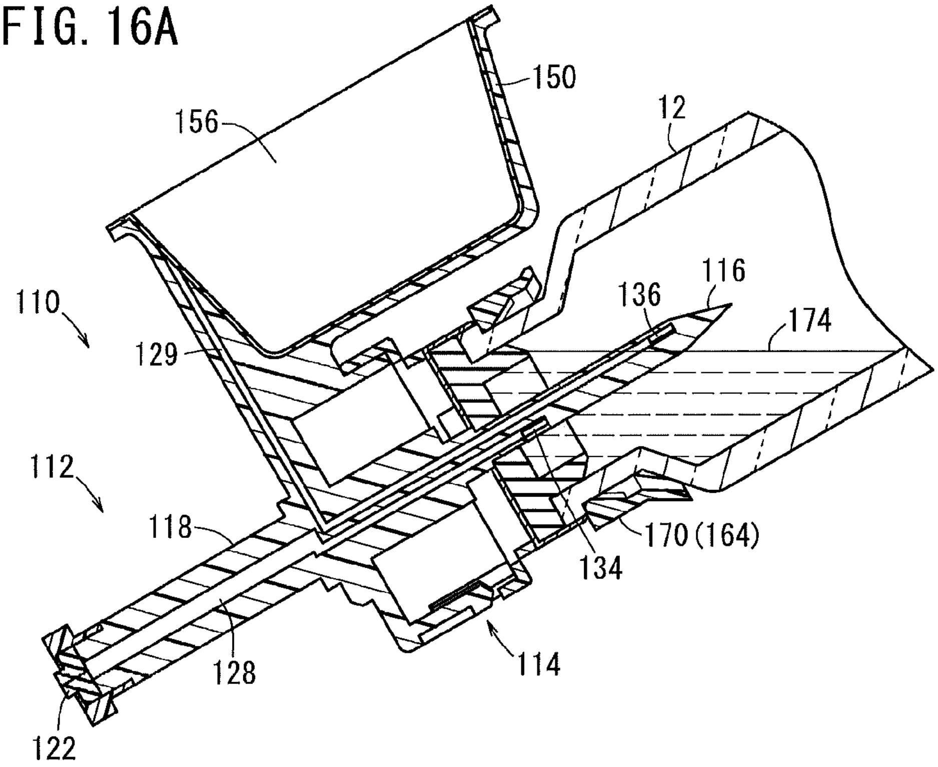
FIG. 16A is a longitudinal sectional view showing an example of a method of recovering a liquid chemical from a vial by use of a vial adapter.

After the drug has been dissolved in or diluted with the liquid transferred from the syringe 80, and the liquid chemical is thereby prepared, the vial 12 together with the vial adapter 110 is inverted or turned upside down. Stated otherwise, as shown in FIG. 16A, a condition is established in which the vial 12 is located on the upper side and the vial adapter 110 is located on the lower side, and the pusher of the syringe 80 is pulled. As a result, the liquid chemical in the vial 12 is moved into the syringe 80 through the first passage 128 in the vial adapter 110. In this instance, the air in the pressure buffer portion 150 is moved into the vial 12, in an amount corresponding to the volume of the liquid chemical flowing out of the vial 12, through the second passage 129, so that the expansion portion 156 becomes deflated (the expansion portion 156 is displaced to the side of the balloon housing 154).

When the vial 12 together with the vial adapter 110 has been inverted or turned upside down, and the pusher of the syringe 80 is pulled in a condition in which the vial 12 is located on the upper side and the vial adapter 110 is located on the lower side, the first side hole 134 is positioned within the liquid chemical. In addition, the second side hole 136, which is disposed in the vicinity of the needle point of the needle 116 while being spaced from the first side hole 134 by the distance X, is located on the upper side. More specifically, the second side hole 136 is positioned above the liquid surface 174 of the liquid chemical (and positioned within the layer of air inside the vial 12). In this instance, air having moved from the expansion portion 156 through the second passage 129 into the vial can, at the time of flowing into the vial 12 through the second side hole 136, flow to the upper side of the liquid surface 174 of the liquid chemical (into the layer of air inside the vial 12) without directly contacting the liquid chemical inside the vial 12. Accordingly, bubbling of the drug due to air flowing into the vial 12 can be restrained.

Figure 16B:
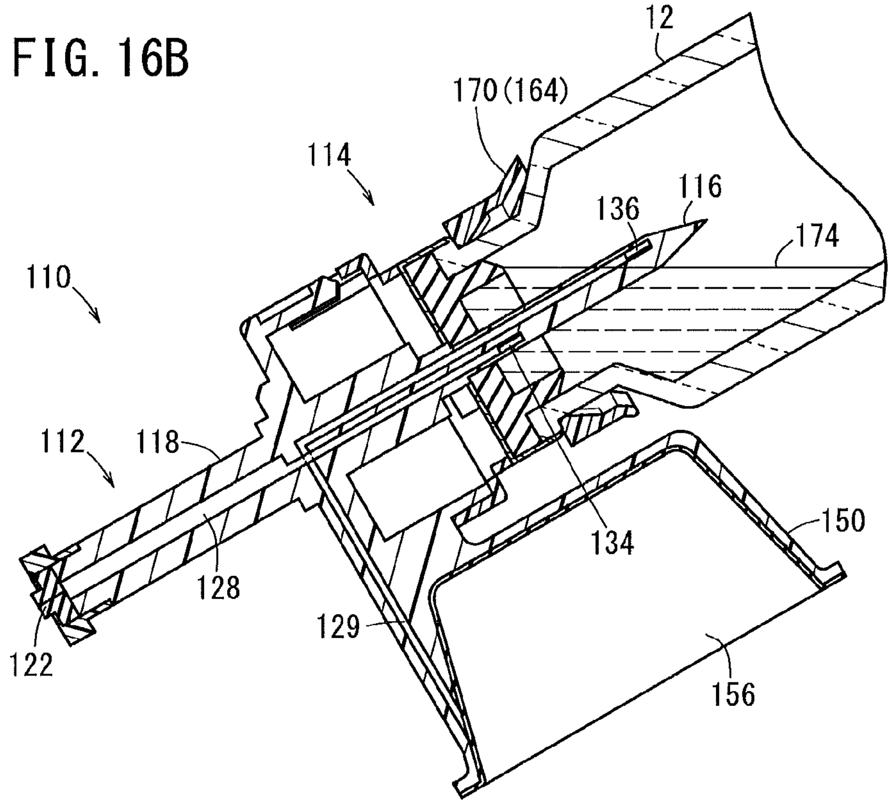
FIG. 16B is a longitudinal sectional view showing another example.

In addition, as mentioned above, the identification portion, which is indicative of the position of the second side hole 136, is disposed in the vicinity of the second side hole 136. Therefore, at the time of inverting the vial 12 upside down together with the vial adapter 110, it is easy to dispose the second side hole 136 above the liquid surface 174 of the liquid chemical (within the layer of air inside the vial 12). Further, if the second side hole 136 is provided on the circumferential surface of the needle 116 farthest from the pressure buffer portion 150, as in a modification shown in FIG. 16B, the second side hole 136 can be more easily disposed above the liquid surface 174 of the liquid chemical.

When the fitting portion 130 is fitted onto the head portion 13 of the vial 12, the region of the first side hole 134 most proximate to the proximal end side is positioned either at roughly the same position as the back surface of the stopper 16, or inside of the stopper 16. Therefore, when the vial 12 is inverted or turned upside down together with the vial adapter 110, the liquid chemical in the vicinity of the back surface of the stopper 16 flows into the first passage 128 through the first side hole 134 located at the position of the back surface of the stopper 16. Accordingly, the amount of liquid chemical left inside the vial 12 can be reduced almost to zero.

Thus, the vial adapter 110 according to the present embodiment is configured so that the position of the second side hole 136 can be optimized, so as to prevent bubbling of the liquid chemical inside the vial 12, and so that the position of the first side hole 134 inside the vial 12 can be optimized. Therefore, the liquid chemical in the vial 12 can be drawn into the syringe 80 while leaving only a miniscule amount of liquid chemical inside the vial 12. Thus, the amount of liquid chemical that is wasted can be reduced.

Third Embodiment

Figure 17:
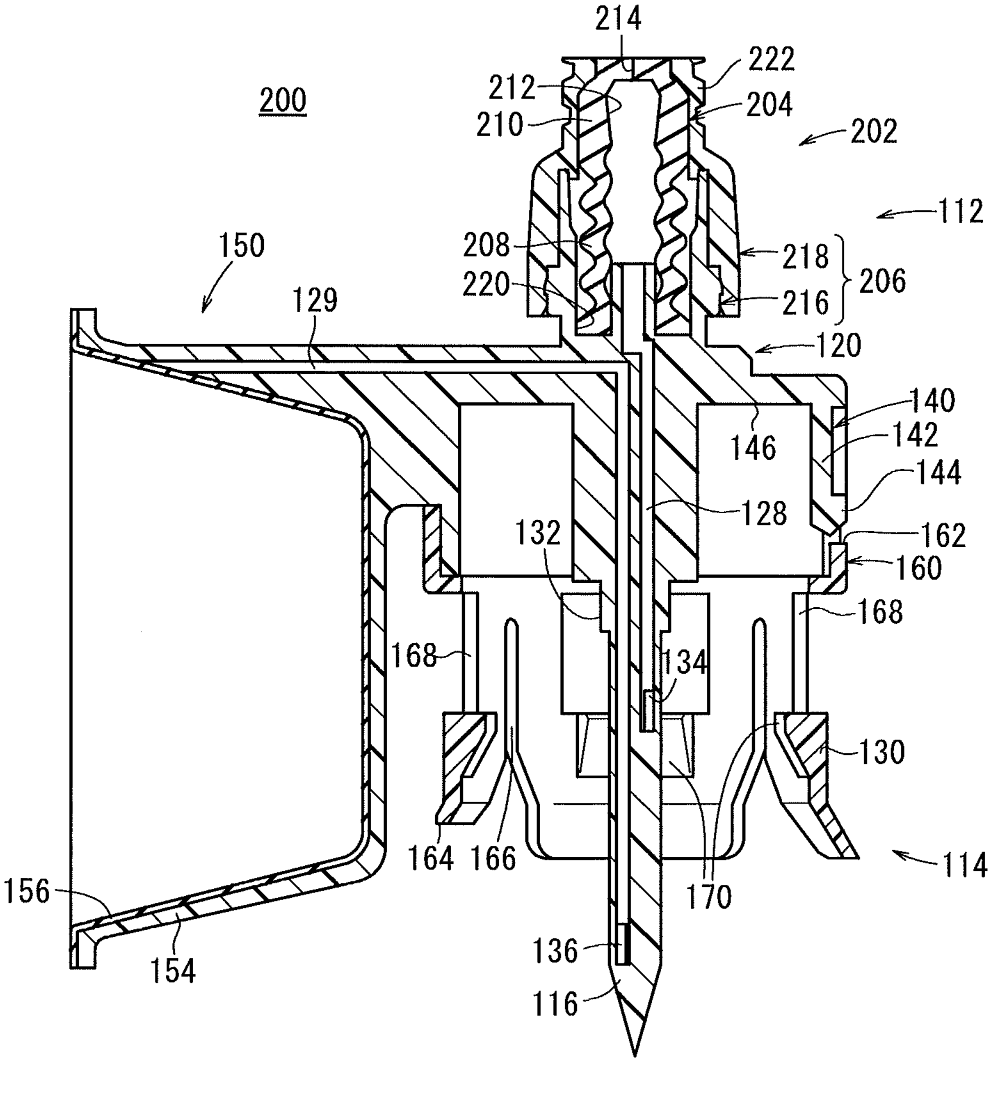
FIG. 17 is a longitudinal sectional view of a vial adapter according to a third embodiment of the present invention.

Next, a third embodiment of the vial adapter according to the present invention will be described below with reference to the drawings. FIG. 17 is a longitudinal sectional view of a vial adapter 200 according to the third embodiment.

As shown in FIG. 17, the vial adapter 200 according to the third embodiment has a configuration in which the connector 118 and the valve body 122 of the vial adapter 110 in the second embodiment are replaced by a different connector 202 and a different valve body 204. Therefore, the connector 202 and the valve body 204 will be described herein, whereas parts that are common to both the vial adaptor 200 and the vial adaptor 110 of the second embodiment above are denoted by the same reference characters as used above, and overlapping descriptions of such parts are omitted.

The connector 202 of the vial adapter 200 includes the valve body 204, and a connector housing 206 in which the valve body 204 is contained (disposed).

The valve body 204 is composed of an elastic member (flexible material) capable of elastic deformation, and has a barrel portion 208 and a head portion 210. The barrel portion 208 is provided with an inner cavity 212 through which a liquid can pass, and a planar top surface of the head portion 210 is provided with a slit 214 that reaches into the inner cavity 212. In addition, the barrel portion 208 is composed of a bellows-like tubular body. Such a barrel portion 208 functions as a biasing means for biasing the valve body 204 from the proximal end side toward the distal end side thereof.

The connector housing 206 has a housing portion 216 and a cover portion 218. The housing portion 216 is formed with a circular groove 220, and a proximal end portion of the valve body 204 is inserted into the circular groove 220. The cover portion 218 is provided therein with a space for containing the valve body 204, and is connected to a distal end portion of the housing portion 216. The cover portion 218 is formed on the outer circumference thereof with a male screw portion 222 for screw engagement with a female screw formed at a connection port 81 (see FIG. 6) provided at the distal end of the syringe 80.

The vial adapter 200 according to the third embodiment of the present invention basically is constituted as described above. Next, operations and effects of the vial adapter 200 will be described below. Incidentally, the vial adapter 200 according to the third embodiment differs from the vial adapter 110 of the second embodiment only in relation to operations and effects thereof at the time of connection between the vial adapter 200 and the syringe 80. Therefore, in the following description, operations and effects at the time of connection between the vial adapter 200 and the syringe 80 will be described, whereas descriptions of operations and effects that are the same or equivalent to those of the vial adapter 110 of the second embodiment will be omitted.

A fitting portion 130 of the vial adapter 200 according to the third embodiment of the present invention is connected to the head portion 13 of a vial 12, and thereafter, a connection port 81 provided at a distal end portion of the syringe 80 is brought into screw engagement with the connector 202, whereby the vial adapter 200 and the syringe 80 are connected to each other. In this instance, the valve body 204 of the connector 202 is pressed by the distal end portion of the syringe 80, and is compressed and deformed in the axial direction. Such deformation causes the slit 214 of the valve body 204 to open, resulting in the syringe 80 and the vial 12 coming into communication with each other through a first passage 128 provided inside the vial adapter 200.

The valve body 204 continues to bias the slit 214 until the bellows-like tubular body of the barrel portion 208 is compressively deformed by the distal end portion of the syringe 80 and until screw engagement of the syringe 80 is effected, whereby external leakage of the liquid chemical in the vial 12 connected through the first passage 128 can securely be prevented.

Thus, the vial adapter 200 according to the present embodiment is configured so that the position of the second side hole 136 can be optimized to thereby prevent bubbling of the liquid chemical inside the vial 12, and so that the position of the first side hole 134 inside the vial 12 can be optimized. Further, until connection of the syringe 80 is made, leakage of the liquid chemical inside the vial 12 to the exterior can be prevented more assuredly. Accordingly, the liquid chemical inside the vial 12 can be recovered into the syringe 80 more assuredly and safely.

While the present invention has been described above in connection with preferred embodiments thereof, the invention is not restricted to the above embodiments. It is a matter of course that various alterations could be adopted without departing from the scope and gist of the present invention.

The invention claimed is:

1. A vial adapter comprising:

a fitting portion, which has a flexible arm portion provided with a claw for engagement with a head portion of a vial and which can be fitted onto the head portion of the vial; and a hollow needle, which is disposed inside the fitting portion coaxially with the fitting portion, and which, when the fitting portion is fitted onto the head portion of the vial, pierces a stopper formed of an elastic material and that is mounted to the vial, and a hollow, tubular reduced-diameter adapter that can be mounted inside the fitting portion, wherein:

a first reduced-diameter fitting portion, which is capable of being fitted onto a vial head portion having a first outside diameter smaller than a basic outside diameter with which the fitting portion can cope, is provided on one end side of the reduced-diameter adapter, and a first claw portion is provided on the inner circumferential side of the first reduced-diameter fitting portion;

a second reduced-diameter fitting portion, which is capable of being fitted onto a vial head portion having a second outside diameter smaller than the first outside diameter, is provided on the other end side of the reduced-diameter adapter, and a second claw portion is provided on the inner circumferential side of the second reduced-diameter fitting portion;

the vial adapter is provided therein with an adapter end insertion portion into which an end portion of the reduced-diameter adapter is inserted when the reduced-diameter adapter is mounted to the fitting portion; and the reduced-diameter adapter can be mounted to the fitting portion in an orientation for enabling insertion of the first reduced-diameter fitting portion into the adapter end insertion portion, and can be mounted to the fitting portion in an orientation for enabling insertion of the second reduced-diameter fitting portion into the adapter end insertion portion.

2. The vial adapter according to claim 1, wherein:

the fitting portion and the needle are configured as separate parts, and the fitting portion is formed of a material that is softer than a material constituting the needle.

3. The vial adapter according to claim 1, wherein the fitting portion is provided in a side portion thereof with a window into which part of an outer circumferential portion of the head portion of the vial is inserted when the fitting portion is fitted onto the head portion of the vial.

4. The vial adapter according to claim 1, wherein:

the reduced-diameter adapter is provided on one end side thereof with a first engaging portion operative to engage with the claw when the reduced-diameter adapter is mounted to the fitting portion in an orientation for enabling insertion of the second reduced-diameter fitting portion into the adapter end insertion portion; and the reduced-diameter adapter is provided on the other end side thereof with a second engaging portion operative to engage with the claw when the reduced-diameter adapter is mounted to the fitting portion in an orientation for enabling insertion of the first reduced-diameter fitting portion into the adapter end insertion portion.

5. The vial adapter according to claim 4, wherein the distance from the first engaging portion of the reduced-diameter adapter to an end face of the other end of the reduced-diameter adapter and the distance from the second engaging portion of the reduced-diameter adapter to an end face of the one end of the reduced-diameter adapter are slightly shorter than the distance from the claw to a deepest region of the adapter end insertion portion.

6. The vial adapter according to claim 1, wherein the reduced-diameter adapter is provided, between the first claw portion and the second claw portion, with a partition wall formed with an opening portion, which is sized to permit insertion of the needle therein, and which is smaller than the first outside diameter.

7. The vial adapter according to claim 1, wherein the needle is provided at a proximal end portion thereof with a stopper contact portion, which abuts on a top surface of the stopper when the fitting portion is fitted onto the head portion of the vial, and when the fitting portion is fitted onto the head portion of the vial, the stopper contact portion abuts on the top surface of the stopper and the claw engages with the head portion of the vial, whereby the fitting portion is fixed to the head portion of the vial.

8. The vial adapter according to claim 7, wherein when the fitting portion is fitted onto the head portion of the vial, a region of the side hole nearest the proximal end of the needle is positioned either roughly at a back surface of the stopper or inside of the stopper.

9. The vial adapter according to claim 8, wherein the needle is provided with a groove portion extending from the region of the side hole nearest the distal end of the needle toward a needle point of the needle.

* * * * *